United States Patent [19]
Riordan et al.

[11] Patent Number: 5,543,399
[45] Date of Patent: Aug. 6, 1996

[54] CYSTIC FIBROSIS TRANSMEMBRANE CONDUCTANCE REGULATOR (CFTR) PROTEIN

[75] Inventors: John R. Riordan, Toronto; Christine E. Bear, North York; Mohabir Ramjeesingh, Mississauga; Canhui Li, Toronto, all of Canada

[73] Assignee: HSC Research & Development Limited Partnership, Canada

[21] Appl. No.: 290,935

[22] PCT Filed: Feb. 17, 1993

[86] PCT No.: PCT/CA93/00065
  § 371 Date: Oct. 13, 1994
  § 102(e) Date: Oct. 13, 1994

[87] PCT Pub. No.: WO93/17040
  PCT Pub. Date: Sep. 2, 1993

Related U.S. Application Data

[63] Continuation-in-part of Ser. No. 123,864, Sep. 20, 1993, which is a continuation of Ser. No. 401,609, Aug. 31, 1989, abandoned, which is a continuation-in-part of Ser. No. 399,945, Aug. 24, 1989, abandoned, which is a continuation-in-part of Ser. No. 396,894, Aug. 22, 1989, abandoned.

[30] Foreign Application Priority Data

Feb. 20, 1992 [CA] Canada .................................. 2061579

[51] Int. Cl.[6] .......................... A61K 38/17; A61K 9/127; C07K 1/36; C07K 14/435
[52] U.S. Cl. .................... 514/21; 514/8; 514/12; 514/851; 530/350; 530/415; 530/417; 424/450
[58] Field of Search ................................. 530/350, 415, 530/417; 514/12, 21, 851, 8; 424/450

[56] References Cited

U.S. PATENT DOCUMENTS

| | | | |
|---|---|---|---|
| 4,322,274 | 3/1982 | Wilson et al. | 204/6 |
| 4,844,893 | 7/1989 | Honsik et al. | 424/85.2 |
| 4,847,201 | 7/1989 | Kaswasaki et al. | 435/69.5 |
| 4,853,331 | 8/1989 | Hermstadt et al. | 435/252.3 |
| 4,861,589 | 8/1989 | Ju | 424/277.1 |
| 4,861,719 | 8/1989 | Miller | 435/236 |
| 4,868,116 | 9/1989 | Morgan et al. | 435/240.2 |
| 4,980,286 | 12/1990 | Morgan et al. | 435/172.3 |
| 5,240,846 | 8/1993 | Collins et al. | 435/240.1 |

FOREIGN PATENT DOCUMENTS

| | | |
|---|---|---|
| 0226288 | 6/1987 | European Pat. Off. . |
| 0288299 | 10/1988 | European Pat. Off. . |
| 0446017 | 9/1991 | European Pat. Off. . |
| 2203742 | 10/1988 | United Kingdom . |
| WO91/02796 | 3/1991 | WIPO . |
| WO91/10734 | 7/1991 | WIPO . |
| WO92/05252 | 4/1992 | WIPO . |
| WO92/05273 | 4/1992 | WIPO . |

OTHER PUBLICATIONS

Bear et al., Purification and Functional Reconstitution of the Cystic Fibrosis Transmembrane Conductance Regulator (CFTR), *Cell* 68:809–818 (1992).

Rommens et al., cAMP—Inducible Chloride Conductance in Mouse Fibroblast Lines Stably Expressing the Human Cystic Fibrosis Transmembrane Conductance Regulator, *Proc. Natl. Acad. Sci. USA* 88:7500–7504 (1991).

Kartner et al., Expression of the Cystic Fibrosis Gene in Non–Epithelial Invertebrate Cells Produces a Regulated Anion Conductance, *Cell* 64:681–691 (1991).

Zielenski et al., Genomic DNA Sequence of the Cystic Fibrosis Transmembrane Conductance Regulator (CFTR) Gene, *Genomics* 10:214–228 (1991).

Drum et al., Correction of the Cystic Fibrosis Defect in Vitro by Retrovirus–Mediated Gene Transfer, *Cell* 62:1227–1233 (1990).

(List continued on next page.)

*Primary Examiner*—Mindy Fleisher
*Assistant Examiner*—Nancy J. Degen
*Attorney, Agent, or Firm*—Bell, Seltzer, Park & Gibson, P.A.

[57] ABSTRACT

A substantially homogeneous protein having cystic fibrosis transmembrane conductance regulator activity is provided. Also provided is a therapeutically effective composition for treating a subject having cystic fibrosis.

15 Claims, 11 Drawing Sheets

OTHER PUBLICATIONS

Quinton, P. M., Cystic Fibrosis: A Disease in Electrolyte Transport, FASEB J. 4:2709–2717 (1990).

The Cystic Fibrosis Genetic Analysis Consortium, Worldwide Survey of the ΔF508 Mutation–Report from the Cystic Fibrosis Genetic Analysis Consortium, Am. J. Hum. Genet. 47:354–359 (1990).

Venglarik et al., a Simple Assay for Agonist–Regulated Cl and K Conductances in Salt–Secreting Epithelial Cells, Am. J. Physiol. 259:C358–C364 (1990).

Kerem et al., Identification of Mutations in Regions Corresponding to the Two Putative Nucleotide (ATP)—Binding Folds of the Cystic Fibrosis Gene, Proc. Natl. Acad. Sci. USA 87:8447–8451 (1990).

Green et al., Chromosomal Region of the Cystic Fibrosis Gene in Yeast Artificial Chromosomes: A Model for Human Genome Mapping, Science 250:94–98 (1990).

Cliff et al., Separate Cl Conductances Activated by cAMP and $Ca^{2+}$ in Cl–Secreting Epithelial Cells, Proc. Natl. Acad. Sci. USA 87:4956–4960 (1990).

Welsh, M. J., Abnormal Regulation of Ion Channels in Cystic Fibrosis Epithelia, FASEB J. 4:2718–2725 (1990).

Hyde et al., Structural Model of ATP—Binding Proteins Associated with Cystic Fibrosis, Multidrug Resistance and Bacterial Transport, Nature 346:362–365 (1990).

Cutting et al., A Cluster of Cystic Fibrosis Mutations in the first Nucleotide–Binding Fold of the Cystic Fibrosis Conductance Regulator Protein, Nature 346:366–369 (1990).

Slot et al., No Evidence for Expression of the Insulin–Regulatable Glucose Transporter in Endothelial Cells, Nature 346:369–371 (1990).

Dean et al., Multiple Mutations in Highly Conserved Residues are Found in Mildly Affected Cystic Fibrosis Patients, Cell 61:863–370 (1990).

Wilson, et al., Correction of CD18—Deficient Lymphocytes by Retrovirus–Mediated Gene transfer, Science 248:1413–1416 (1990).

Schoumacher et al., A Cystic Fibrosis Pancreatic Adenocarcinoma Cell Line, Proc. Natl. Acad. Sci. USA 87:4012–4016 (1990).

White et al., A Frame–Shift Mutation in the Cystic Fibrosis Gene, Nature 344:665–667 (1990).

Wilson et al., Expression of Human Adenosine Deaminase in Mice Reconstituted with Retrovirus–Transduced hamatopoietic Stem Cells, Proc. Natl. Acad. Sci. USA 87:439–443 (1990).

Boat et al., Cystic Fibrosis in The Metabolic Basis of Inherited Disease, vol. II, (Scriver et al., eds.) McGraw–Hill Information Services Company, N.Y., N.Y., pp. 2649–2679 (1989).

Sanbrook et al., Oligonucleotide–Mediated Mutagendsis in Molecular Cloning, A Laboratory Manual, 2nd Ed., Cold Spring Harbor Press, Cold Spring Harbor, NY, pp. 15.51–15.80 (1989).

Fulton et al., A 12 Megabase Restriction Map at the Cystic Fibrosis Locus, Nucleic Acids Research 17(1):271–284 (1989).

Dean et al., Approaches to Localizing Disease Genes as Applied to Cystic Fibrosis, Nucleic Acids Research 18(2):345–350 (1989).

Rommens et al., Physical Localization of Two DNA Markers Closely Linked to the Cystic Fibrosis Locus by Pulsed–Field Gel Electrophoresis, Am. J. Hum. Genet. 45:932–941 (1989).

Kerem et al., DNA Marker Haplotype Association with Pancreatic Sufficiency in Cystic Fibrosis, Am. J. Hum. Genet. 44:827–834 (1989).

Estivill et al., Isolation of a New DNA Marker in Linkage Disequilibrium with Cystic Fibrosis, Situated Between J3.11 (D7s8) and IRP, Am. J. Hum. Genet. 44:704–710 (1989).

Iannuzzi et al., Isolation of Additional Polymorphic Clones from the Cystic Fibrosis Region, Using Chromosome Jumping from D7s8, Am. J. Hum. Genet. 44:695–703 (1989).

Beaudet et al., Linkage Disequilibrium, Cystic Fibrosis and Genetic Counseling, Am. J. Hum. Genet. 44:319–326 (1989).

Smith et al., Cystic Fibrosis: Diagnostic Testing and the Search for the Gene, Clin. Chem. 35/7(B):B17–B20 (1989).

Jensen et al., Chloride Channel Expression in Cultures of Sweat Gland Epithelial Cells in cystic Fibrosis, J. Cell. Biol. 107(6):139a, Abstract No. 788 (1989).

Orr et al., In Vivo and In Vitro Phosphorylation of Apical Membrane Proteins of the T–84 Colonic Epithelial Cell Line, J. Cell Biol. 107(6):493a, Abstract No. 2776 (1989).

Willumsen et al., Activation of an Apical Cl' Conductance by $Ca^{2+}$ Ionophores in Cystic Fibrosis Airway Epithelia Am. J. Physiol. 256: C226–C233 (1989).

Chen et al., A cAMP—Regulated Chloride Channel in Lymphocytes That is Affected in Cystic Fibrosis, Science 243:657–660 (1989).

Tabcharani et al., Bicarbonate Permeability of the Outwardly Rectifying Anion Channel, J. Membrane Biol. 112:109–122 (1989).

Scholte et al., Immortalization of Nasal Polyp Epithelial Cells from Cystic Fibrosis Patients, Experimental Cell Research 182:559–571 (1989).

Koshland, D. E., Jr., The Cystic Fibrosis Gene Story, Science 245(4922); 1029 (1989).

Riordan et al., Identification of the Cystic Fibrosis Gene: Cloning and Characterization of Complementary DNA, Science 245:1066–1073 (1989).

Mark, J. L., The Cystic Fibrosis Gene is Found, Science 245:923–925 (1989).

Corey et al., Familial Concordance of Pancreatic Function in Cystic Fibrosis, Journal of Pediatrics 115(2):274–277 (1989).

Kerem et al., Identification of the Cystic Fibrosis Gene: Genetic Analysis, Science 245:1073–1080 (1989).

Rommens et al., Identification of the Cystic Fibrosis Gene: Chromosome Walking and Jumping, Science 245:1059–1065 (1989).

Cheng et al., Increased Sulfation of Gycoconjugates by Cultured Nasal Epithelial Cells from Patients with Cystic Fibrosis, J. Clin. Invest. 84:68–72 (1989).

Jetten et al., Persistence of Abnormal Chloride Conductance Regulation in Transformed Cystic Fibrois Epithelia, Science 244:1472–1475 (1989).

Landry, et al., Purification and Reconstitution of Chloride Channels from Kidney and Trachea, Science 244:1469–1472 (1989).

Drumm et al., Physical Mapping of the Cytic Fibrosis Region by Pulsed–Field Gel Electrophoresis, Genomics 2:346–354 (1988).

Poustka et al., a Long–Range Restriction Map Encompassing the Cystic Fibrosis Locus and Its Closely Linked Genetic Markers, Genomics 2:337–345 (1988).

Tsui et al., Progress Towards Cloning the Cystic Fibrosis Gene, Phil. Trans. R. Soc. Lond. B319:263–273 (1988).

Rommens et al., Genetic and Physical Mapping of the Chromosomal Region Containing the Cystic Fibrosis Locus, *Am J. Hum. Genetics* 43(3 Suppl.):A199 (1988).

Rommens et al., Identification and Regional Localization of DNA Markers on Chromosome 7 for the Cloning of the Cystic Fibrosis Gene, *Am. J. Hum. Genet.* 43:645–663 (1988).

Farrall et al., Recombinations Between IRP and Cystic Fibrosis, *Am. J. Hum. Genet.* 43:471–475 (1988).

Dean, M., Molecular and Genetic Analysis of Cystic Fibrosis, *Genomics* 3:93–99 (1988).

Riordan et al., Molecular Studies of Cultured Epithelial Cells from the Sweat Gland in Cellular and Molecular Basis of Cystic Fibrosis, (G. Mastella and P. M. Quinton, Eds.) San Francisco Press, Inc., San Francisco, CA, pp. 416–424 (1988).

Reddy et al., Electrical properties of Cultured Reabsorbtive Sweat Duct Cells from Normal and Cystic . . . in Cellular and Molecular Basis of Cystic Fibrosis (G. Mastella and P. M. Quinton, Eds.) San Francisco Press, Inc., San Francisco Press, Inc., San Francisco, CA, pp. 383–393 (1988).

Short et al., λZAP: A Bacteriophage λ Expression Vector with In Vivo Excision Properties, *Nucleic Acids Research* 16(15):7583–7600 (1988).

Reddy et al., Retention of Basic Electrophysiologic Properties by Human Sweat Duct Cells in Primary Culture, *In Vitro Cellular & Developmental Biology* 24(9):905–910 (1988).

Dodge, J. A., Implications of the New Genetics for Screening for Cystic Fibrosis, *The Lancet;* 672–673 (1988).

Wilson et al., Correction of the Genetic Defect in Hepatcytes from the Watanabe Heritable Hyperlipidemic Rabbit, *Proc. Natl. Acad. Sci. USA* 85:4421–4425 (1988).

Li et al., Cyclic AMP—Dependent Protein Kinase Opens Chloride Channels in Normal but not Cystic Fibrosis Airway Epithelium, *Nature* 331:358–360 (1988).

Lathrop et al., Refined Linkage Map of Chromosome 7 in the Region of the Cystic Fibrosis Gene, *Am. J. Hum. Genet.* 42:038–044 (1988).

Harris et al., Establishment of a Tissue Culture System for Epithelial Cells Derived from Human Pancreas: A Model for the Study of Cystic Fibrosis, *Journal of Cell Science* 87:695–703 (1987).

Buchwald et al., Current Status of the Genetics of Cystic Fibrosis in Genetics and Epithelial Cell Dysfunction in Cytic Fibrosis (Alan R. Liss, Inc.), pp. 19–29 (1987).

Buchwald et al., The Genetics of Cystic Fibrosis—Mid 1987, *Excerta Med. Asia Pacific Congress* 743–9 (1987).

Tsui et al., Progress Towards Cloning of the Cystic Fibrosis Gene—Identification of New DNA Markers in the 7Q31 Region, *Protides of the Biological Fluids* 35:51–54 (1987).

Estivill et al., Patterns of Polymorphism and Linkage Disequilibrium for Cystic Fibrosis, *Genomics* 1:257–263 (1987).

Zengerling et al., Mapping of DNA Markers Linked to the Cystic Fibrosis Locus on the Long Arm of Chromosome 7, *Am. J. Hum. Genet.* 40:228–236 (1987).

Beaudet et al., Prenatal Diagnosis of Cystic Fibrosis, *J. Ped.* 111: 630–633 (1987).

Riordan et al., Utilization of Cultured Epithelial Cells from the Sweat Gland in Studies of the CF Defect in Genetics and in Epithelial Cell Dysfunction in Cystic Fibrosis, Alan R. Liss, Inc. pp. 59–71 (1987).

Reddy et al., Lack of β–Adrenergic Responsiveness in Cells Cultured from Reabsorptive Sweat Ducts of Cystic Fibrosis (CF) Subjects, *Pediatric Pulmonology Supp.* 1:115 Abstract No. 31 (1987).

Riordan, J. Reaching Between the Functional and Genetic Defects in Cystic Fibrosis, *Pediatric Pulmonology Suppl.* 1:29 (1987).

Frizell, R. A., Cystic Fibrosis: A Disease of Ion Channels, *TINS* 10(5):190–193 (1987).

Schoumacher et al., Phosphorylation Fails to Activate Chloride Channels from Cystic Fibrosis Airway Cells, *Nature* 330:752–754 (1987).

Meakin et al., τ–Crystallins of the Human Eye Lens: Expression Analysis of Five Members of the Gene Family, *Molecular and Cellular Biology* 7(8): 2671–2679 (1987).

Michiels et al., Derivation of Clones Close to *met* by Preparative Field Inversion of Gel Electrophoresis, *Science* 236:1305–1308 (1987).

Korman et al., Expression of Human Class II Major Histocompatibility Complex Antigens Using Retrovirus Vectors, *Proc. Natl. Acad. Sci. USA* 84:2150–2154 (1987).

Wahl et al., Cosmid Vectors for Rapid Genomic Walking, Restriction Mapping, and Gene Transfer, *Proc. Natl. Acad. Sci. USA* 84:2160–2164 (1987).

Estivill et al., A Candidate for the Cystic Fibrosis Locus Isolated by Selection for Methylation–Free Islands, *Nature* 326:840–845 (1987).

Collins et al., Construction of a General Human Chromosome Jumping Library, with Application to Cystic Fibrosis, *Science* 235:1046–1049 (1987).

Spence et al., Linkage of DNA Markers to Cystic Fibrosis in 26 Families, *Am. J. Hum. Genet.* 39:729–734 (1986).

Tsui et al., Genetic Analysis of Cystic Fibrosis Using Linked DNA Markers, *Am. J. Hum. Genet.* 39:720–728 (1986).

Beaudet et al. Linkage of Cystic Fibrosis to Two Tightly Linked DNA Markers: Joint Report from a Collaborative Study, *Am. J. Hum. Genet.* 39:681–693 (1986).

Scambler et al., Chromosome Mediated Gene Transfer of Six DNA Markers Linked to the Cystic Fibrosis Locus on Human Chromosome Seven, *Nucleic Acids Res.* 14:7159–7174 (1986).

Tsui et al., Mapping of the Cystic Fibrosis Locus on Chromosome 7, *Cold Spring Harbor Symp. Quant. Biol.* LI:325–335 (1986).

Schmiegelow et al., Linkage Between the Loci for Cystic Fibrosis and Paraoxonase, *Clinical Genetics* 29:374–377 (1986).

Buchwald et al., Linkage of Cystic Fibrosis to the proα2(I) Collagen Gene, COL1A2, on Chromosome 7, *Cytogenet Cell Genet.* 41:234–239 (1986).

Boucher et al., $Na^+$ Transport in Cystic Fibrosis Respiratory Epithelia, *J. Clin. Invest.* 78:1245–1252 (1986).

Frizzell et al., Altered Regulation of Airway Epithelial Cell Chloride Channels in Cystic Fibrosis, *Science* 233:558–560 (1986).

Welsh et al., Chloride and Potassium Channels in Cystic Fibrosis Airway Epithelia, *Nature* 322:467–470 (1986).

Tsui et al., Cystic Fibrosis: Progress in Mapping the Disease Locus Using Polymorphic DNA Markers. I., *Cytogenet. Cell Genet.* 39:299–301 (1985).

Knowlton et al., A Polymorphic DNA Marker Linked to Cystic Fibrosis is Located on Chromosome 7, *Nature* 318(6044):380–382 (1985).

Yankaskas et al., Culture of Human Nasal Epithelial Cells on Collagen Matrix Supports, *Am. Rev. Respir. Dis.* 132:1281–1287 (1985).

Smith, M., In Vitro Mutagenesis, *Ann. Rev. Genet.* 19:423–462 (1985).

White et al., A Closely Linked Genetic Marker for Cystic Fibrosis, *Nature* 318:382–384 (1985).

Tsui et al., Cystic Fibrosis Locus Defined by a Genetically Linked Polymorphic DNA Marker, *Science* 230:1054–1057 (1985).

Stutts et al., Chloried Uptake into Cultured Airway Epithelial Cells from Cystic Fibrosis Patients and Normal Individuals, *Proc. Natl. Acad. Sci. USA* 82:6677–6681 (1985).

Collie et al., Culture of Sweat Gland Epithelial Cells from Normal Individuals and Patients with Cystic Fibrosis, *In Vitro Cellular & Developmental Biology*, 21(10):597–602 (1985).

Widdicombe et al., Cystic Fibrosis Decreases the Apical Membrane Chloride Permeability of Monolayers Cultured from Cells of Tracheal Epithelium, *Proc. Natl. Acad. Sci. USA* 82:6167–6171 (1985).

Wainwright et al., Localization of Cystic Fibrosis Locus to Human Chromosome 7cen–122, *Nature* 318:384–385 (1985).

Taussig, L. M., Cystic Fibrosis: An Overview, *Cystic Fibrosis* (Taussig, L. M., ed.) Thieme–Stralton, N.Y., N.Y., pp. 1–9 (1984).

Sato et al., Defective Beta Adrenergic Response of Cystic Fibrosis Sweat Glands In Vivo and In Vitro, *J. Clin. Invest.* 73:1763–1771 (1984).

Brock, D. J. H., Amniotic Fluid Alkaline Phosphatase Isoenzymes in Early Prenatal Diagnosis of Cystic Fibrosis, *The Lancet*, pp. 941–943 (1983).

Feinberg et al., A Technique for Radiolabeling DNA Restriction Endouclease Fragments to High Specific Activity, *Analytical Biochemistry* 132:6–13 (1983).

Boat et al., Human Respiratory Tract Secretions, *Archives of Biochemistry and Biophysics* 177:95–104 (1976).

Fiani et al. "Selective Targeting of Drugs" Trendi Biotechnol. 7 57–61 1989.

Ostedgaard et al. "Partial Purification of the Cystic Fibrosis Transmembrane Conductance Regulator" J. Biol. Chem. 267(36) 26142–26149 1992.

Sofer et al. "Designing An Optimal Chromatographic Purification Scheme for Proteins" Bio Techniques 1(4) 198–203 1983.

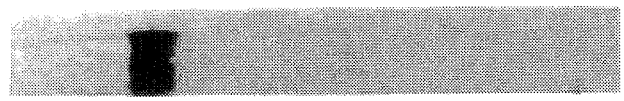
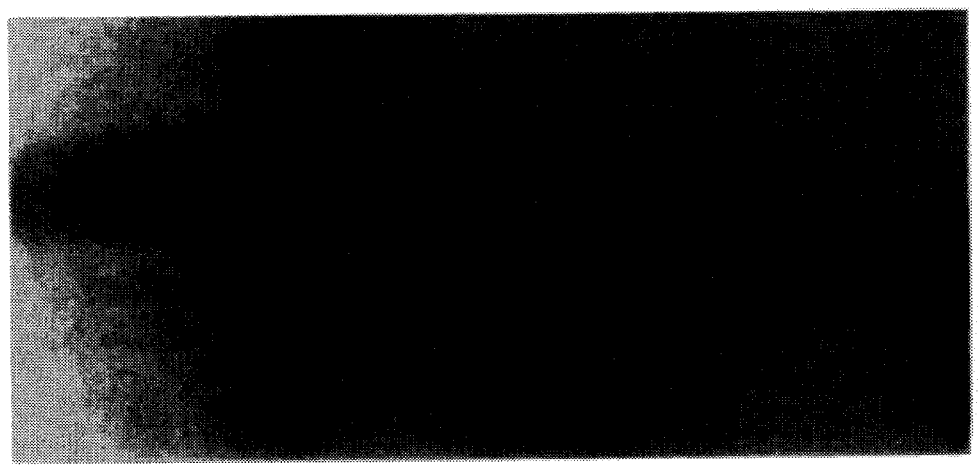
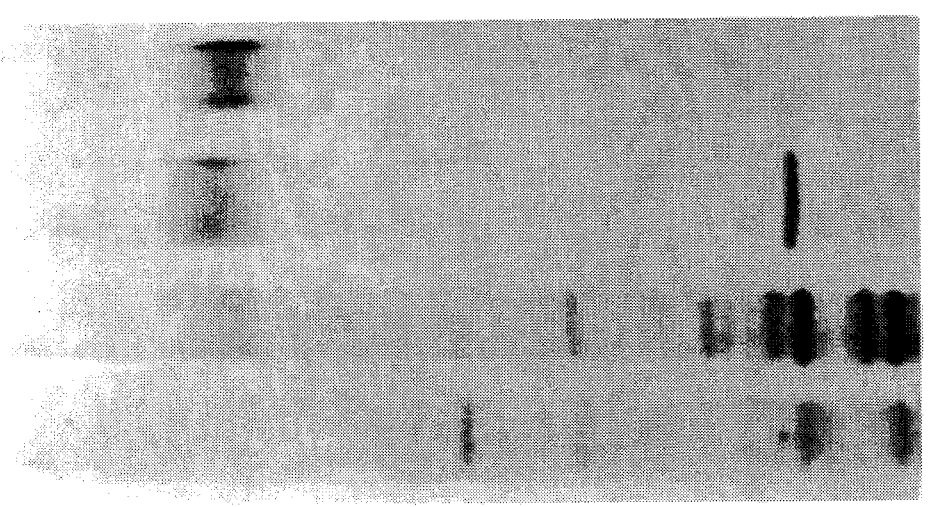
FIG. 1C.
FIG. 1B.
FIG. 1A.

a) NYSTATIN SPIKES AND APPEARANCE OF Cl-
CONDUCTANCE (+CFTR,PKA AND ATP)

b) LIPOSOMES-CFTR + PKA AND ATP c) LIPOSOMES + CFTR -PKA AND ATP d) LIPOSOMES + CFTR + PKA AND ATP 1.0 pA 307.2 ms

CYSTIC FIBROSIS TRANSMEMBRANE CONDUCTANCE REGULATOR (CFTR) PROTEIN

This application is a continuation-in-part of U.S. patent application Ser. No. 08/123,864, filed Sep. 20, 1993, which is a continuation of U.S. application Ser. No. 401,609, filed Aug. 31, 1989, now abandoned, which is a continuation-in-part of U.S. application Ser. No. 07/399,945, filed Aug. 24, 1989, now abandoned, which is a continuation-in-part of U.S. application Ser. No. 07/396,894, filed Aug. 22, 1989, now abandoned.

This invention relates to purified and functionally reconstituted preparations of Cystic Fibrosis Transmembrane Conductance Regulator (CFTR) and to pharmaceutical compositions and methods of use employing these preparations.

The discovery of the gene which is mutated in patients with cystic fibrosis (CF) and the principal disease-causing mutation (Rommens et al., 1989; Riordan et al., 1989; Kerem et al., 1989) has given rise to the possibility of the development of molecular therapies. These can be considered in at least three broad categories: A.) The creation or identification of drugs to appropriately modify CFTR function or biosynthesis; B.) gene therapy by the delivery of the CFTR DNA sequence in an appropriate vector to affected epithelial cells; C.) protein replacement therapy in which the CFTR protein in an appropriate vehicle is delivered to the same cells.

The steps to be accomplished for the effective application of the third strategy 1) the production of large quantities of functional CFTR protein; 2) the solubilization and purification of the CFTR protein; 3) the reconstitution of the homogeneous purified protein into a lipid environment in which it can function; 4) demonstration that the purified and reconstituted CFTR molecule has the same functional properties as it had in the epithelial cells to which it is native; 5) fusion of proteoliposomes containing functional purified CFTR with the apical surfaces of CF epithelial cells expressing nonfunctional mutant CFTR or no CFTR at all in order to restore regulated chloride channel activity.

The original CFTR cDNAs which we had isolated and cloned (Riordan et al., 1989) and deposited with ATCC have been used for expression of CFTR in a number of different heterologous mammalian cell systems (Tabcharani et al., 1991; Anderson et al., 1991a; Cheng et al, 1990; Dalemans et al., 1991). However, because of limitations on the amount of CFTR which can be synthesized in human and other mammalian cells (Cheng et al., 1990; Gregory et al., 1991), it was necessary to utilize an alternative system to generate adequate amounts for purification. We employed the baculovirus expression vector system (BEVS; Lucknow and Summers, 1988) to produce large quantities of functional human CFTR in insect Sf9 cells (Kartner et al., 1991). More recently, others have produced CFTR protein in the milk of transgenic mice (DiTullio et al., 1992) as another potential means of producing sufficient protein for purification. However, in that work no evidence of functionality was demonstrated, nor were any attempts at purification made.

The present invention involves the fulfilment of steps 2.), 3.) and 4.) resulting in the production of highly purified CFTR protein as judged by stringent criteria of homogeneity. The purified protein is further demonstrated to exhibit the same functional properties of a regulated chloride ion channel as it does in its native location in vivo. In addition, as expected, structural features including N-terminal amino acid sequence (6 residues), overall amino acid composition and isoelectric point are identical to those predicted from the translated DNA sequence of the coding region of the cloned CFTR gene. The only feature of the protein produced in the insect cell expression system which differs from that produced in human epithelial cells is the type of carbohydrate added when the protein is glycosylated during synthesis. However, we have already demonstrated that this difference is without influence on the function of the glycoprotein (Kartner et al., 1991). The glycosylation of the protein in any other of the alternate expression systems which may be used such as milk of transgenic animals (DiTullio et al., 1992) will also differ from that in the human lung which will be the principal site of delivery for therapeutic purposes.

The invention also teaches that the proteoliposomes of the type known to be capable of fusing with the membranes of cells, can be fused to planar lipid bilayers in which the generation of electrical currents carried by chloride ions through the CFTR channel can be measured.

In accordance with a further aspect of the invention, there is provided a means of replacement of defective CFTR in the epithelial cells from CF patients by delivery to them of the purified and reconstituted recombinant CFTR protein.

In addition to its direct use in protein replacement therapy, the purified CFTR of the invention provides for the development of alternative therapeutic strategies, for example the development of rationally designed drugs based on features of the molecule's structure which can be determined from the purified preparation.

BACKGROUND OF THE INVENTION

The cloning of the gene mutated in patients with cystic fibrosis (CF) has made possible interpretation of the deduced primary structure of the gene product, CFTR. In the context of what was known of an epithelial $Cl^-$ permeability defect in CF, this lead to the original suggestion that the gene coded for either a $Cl^-$ channel itself or a regulator of a separate $Cl^-$ channel (Riordan et al, 1989). The introduction of expressible CFTR cDNAs into cells bearing CF-causing mutations in the gene (Rich et al, 1990; Druman et al, 1990), or into cells in which CFTR is not normally expressed (Anderson et al, 1991a; Kartner et al, 1991; Rich et al, 1991; Bear et al, 1991; Dalemans et al, 1991; Drumm et al, 1991) resulted in the appearance of a $Cl^-$ conductance regulated by cyclic AMP and similar to that seen in several normal epithelial cell types (Gray et al, 1989; Tabcharani et al, 1990). A low conductance ohmic $Cl^-$ channel activated by protein kinase A (PKA)—catalysed phosphorylation and inactivated by dephosphorylation was shown to underlie this conductance pathway (Tabcharani et al, 1991; Berger et al, 1991). Although these findings cannot distinguish between the CFTR protein constituting the conductance pathway itself, or its being a phosphorylation-activated regulator, changes in ion selectivity on mutation of amino acids with charged side chains in the proposed transmembrane sequences (viz. K95 in TM1 and K335 in TM6; Anderson et ai, 1991b) tend to support the former possibility.

Consistent with its proposed role as an ion channel, CFTR is a relatively non-abundant protein in the epithelial tissues in which it is endogenously expressed. We know of no tissue which provides an adequate source for purification. Similarly, it has not yet been possible to establish mammalian cell lines in which a very high level of heterologous expression of CFTR occurs (Cheng et al, 1990). This is believed to be at least partially due to a rather stringent control of CFTR biosynthesis which limits the amount of wild type protein which accumulates in cells (Gregory et al, 1991). This quality control is apparently more strictly enforced in the case of some mutant forms of CFTR, including the product of the most common mutation (F508), in which little or no mature protein is detectable and only small amounts of immature precursor is present, apparently in the endoplasmic reticulum (Cheng et al, 1990).

Until the work of the present inventors, no one had succeeded in isolating CFTR and purifying it to substantial homogeneity.

BRIEF DESCRIPTION OF THE DRAWINGS

FIG. 1A–1C. Enrichment of CFTR during major steps of purification. Aliquots containing approximately 1 μg of protein were subjected to SDS-PAGE (6% acrylamide in A and B and 4–15% acrylamide in C). Panels A and C show results of silver staining and B is an immunoblot probed with monoclonal antibody M3A7. In 1A and 1B, lane 1 is the initial crude particulate fraction; lane 2, the same fraction after alkali extraction of peripheral membrane proteins; lane 3, the highly enriched peak 'F' from hydroxyapatite; lane 4, the CFTR-containing fraction of the final Superose 6 step. In panel C only the final gel filtration purified fraction was run.

DESCRIPTION OF THE INVENTION

The inventors showed previously (Kartner et al, 1991) that large amounts of functional CFTR can be generated in Sf9 insect cells using the baculovirus expression vector system (BEVS; Luckow and Summers, 1988), thereby providing the starting point for purification. Suspension cultures of these cells have been used to obtain relatively large quantities of a crude CFTR-containing particulate fraction as starting material for purification. Cold alkaline extraction (Steck and Yu, 1973) of the particulate fraction resulted in removal of approximately ⅔ of the total protein while retaining CFTR (Table I; FIG. 1A and B). At this stage a CFTR band was clearly visible by protein staining following SDS-PAGE (FIG. 1A). Our strategy for solubilization and further fractionation employed the strong dissociating conditions of an ionic detergent for two principal reasons. First, systematic testing of the effectiveness of a range of nonionic and ionic detergents to solubilize CFTR in membranes of T84 epithelial cells, CHO cells or Sf9 cells expressing the protein showed that only the stronger ionic ones were effective. Second, because our major aim was to determine whether CFTR could function as a regulated Cl⁻ channel we wished to minimize the possibility of copurification of any proteins which might associate with CFTR and contribute to the function of the final purified material.

Figure 2A:
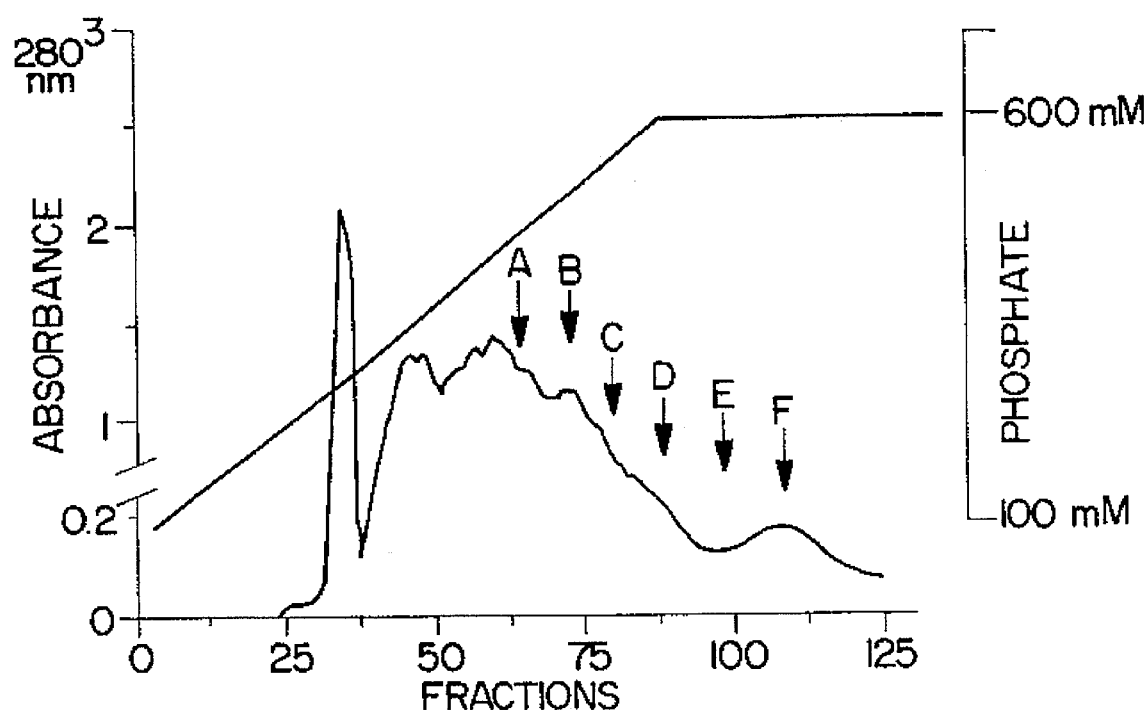
FIGS. 2A–2B. Major purification of CFTR by hydroxyapatite chromatography. The upper panel shows the elution profile with phosphate gradient indicated and the lower panel shows silver staining protein bands after SDS-PAGE of fractions as indicated. Lane F containing most of the CFTR clearly corresponds to lane 3 in panels 1A and 1B of FIG. 1.
Figure 2B:
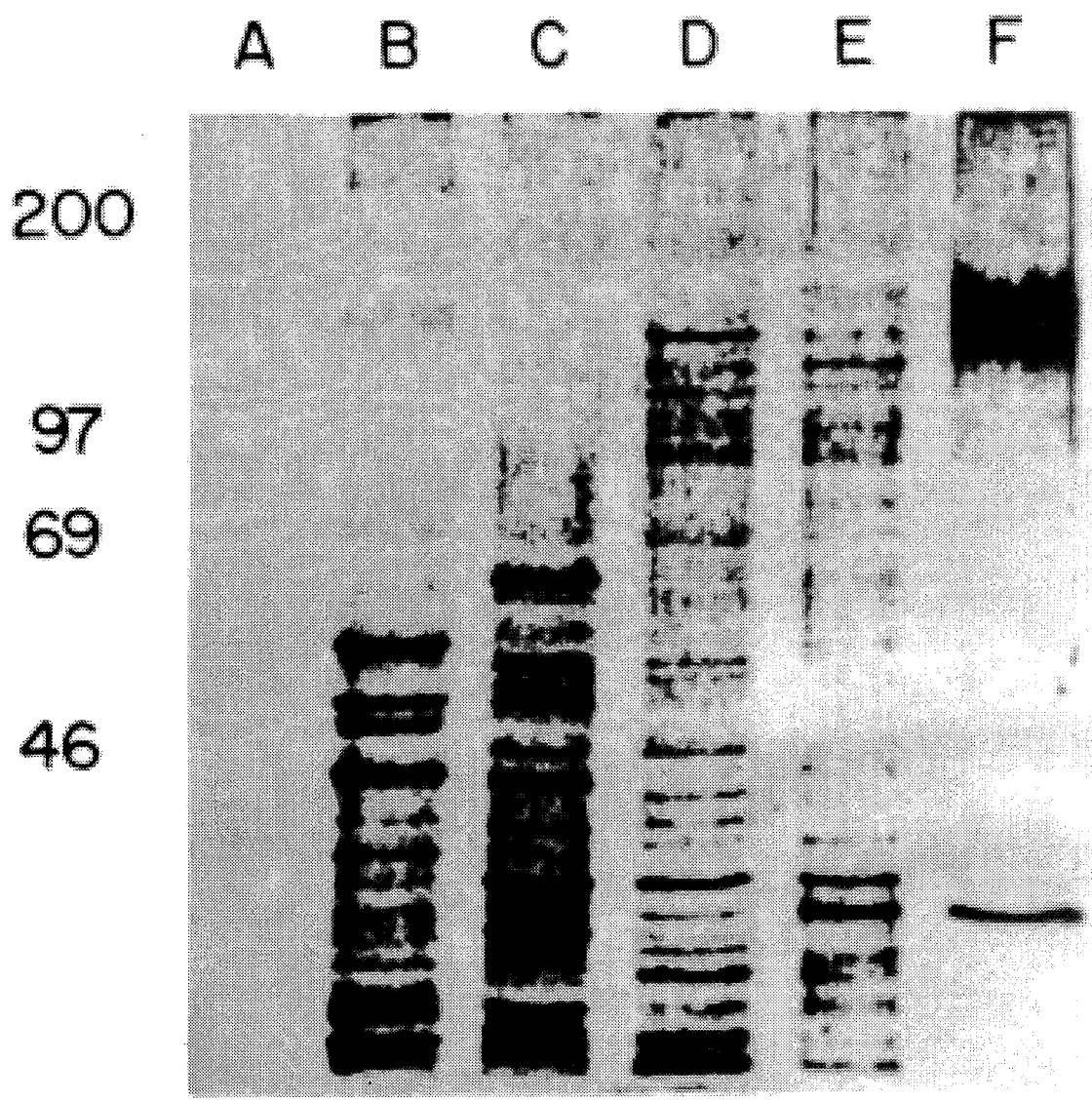
Figure 3:
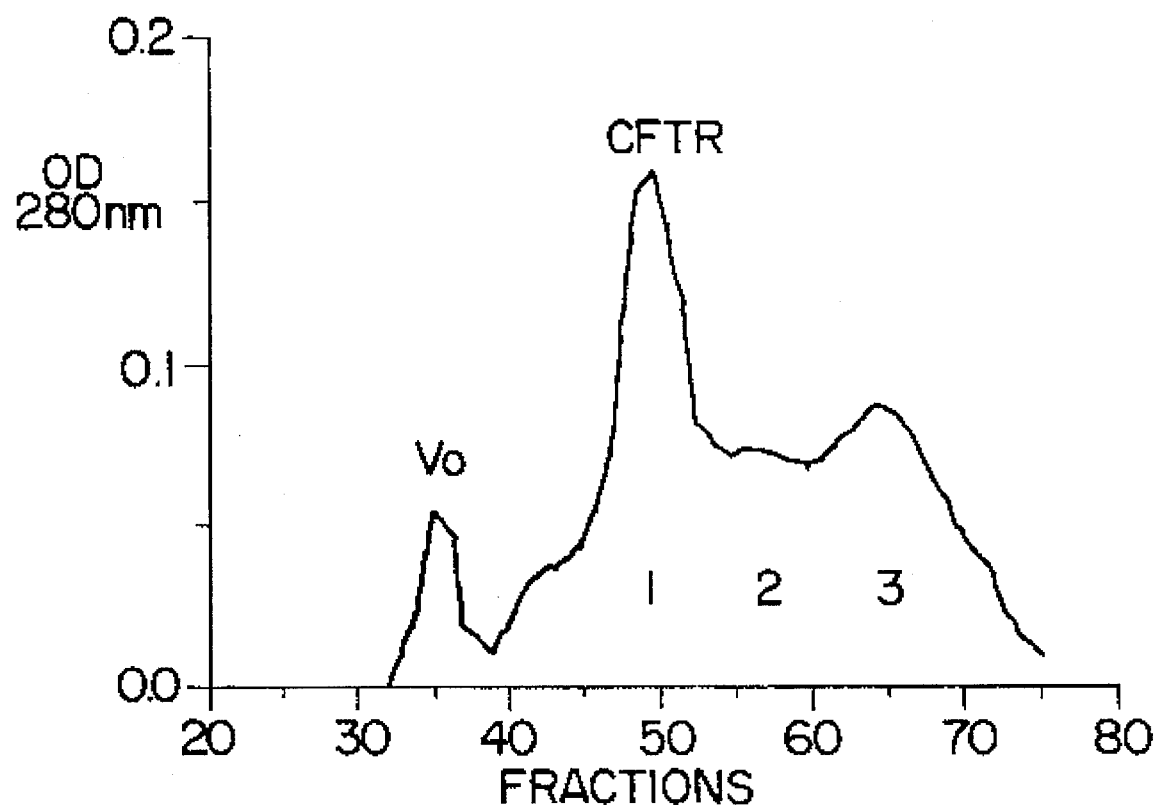
FIG. 3. Gel filtration chromatography on Superose 6 of peak F from FIG. 2. Fractions constituting peak 1 contain highly purified CFTR as indicated in lane 4 of FIG. I A and B, table II and N-terminal sequence analysis.

Conventional column chromatography techniques compatible with the presence of sodium dodecyl sulfate (SDS) (at 0.15 to 0.25%) were then tested for their ability to separate CFTR from other proteins. Among the methods attempted, adsorption to hydroxyapatite proved to be by far the most effective (FIG. 2). CFTR interacted with the matrix more strongly than nearly all other proteins under the conditions employed and was eluted only after the phosphate gradient had reached its maximum concentration of 600 mM. A purification of at least one hundred fold was achieved in this step (Table 1). A major contaminating protein of approximately 30 kd, and very high molecular weight material running at the origin of a 6% acrylamide gel, was also present in this fraction. Minor amounts of faintly silver staining material at molecular weights both lower and higher than the principal CFTR band were also detectable; the immunoblot of this lane indicates that at least some of these are degraded and aggregated forms of CFTR, respectively. CFTR could be separated from the remaining contaminants by gel filtration on Superose 6 (FIG. 3). The protein eluted in a well-resolved included peak corresponding to 28% of the Superose gel volume. From one liter of cells ($5 \times 10^9$) approximately 0.5 mg of CFTR protein was obtained in this peak.

Characterization of purified CFTR

The effectiveness of the major purification steps is summarized in FIG. IA and B. The presence in the final product assessed on 6% SDS-PAGE gels of a single silver staining band reactive with monoclonal antibodies to CFTR indicates that it is not contaminated with other proteins larger than the cutoff molecular weight of the gel. To determine if still smaller proteins might be present a 4–15% gradient gel was heavily loaded and stained with silver (FIG. IC). No other bands were detectible.

Figure 4A:
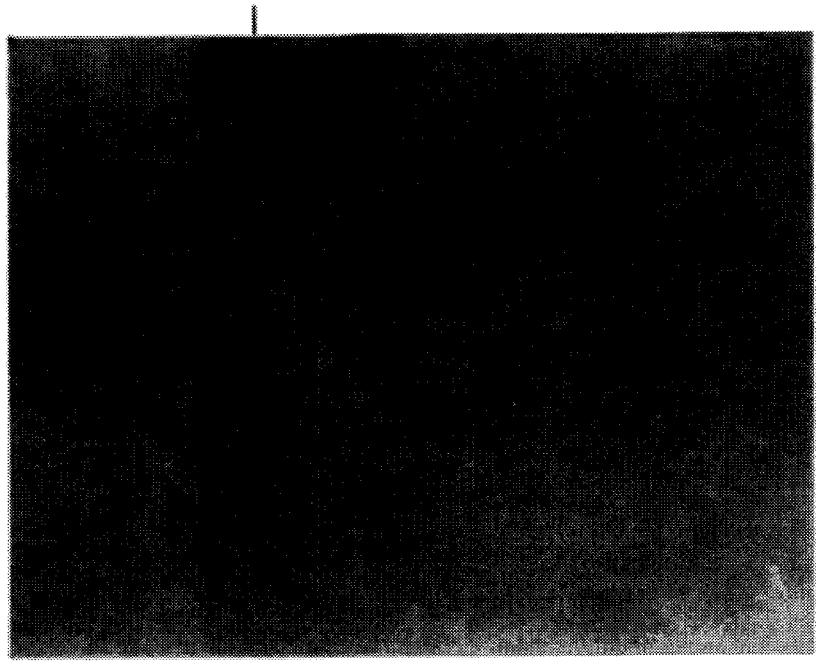
FIGS. 4A–4B. 2-D gel electrophoresis of purified CFTR. For isoelectric focusing 2% ampholytes ranging from pI 3.5 to 10 and 7% acrylamide was used. Electrophoresis was as with 1-D gels as was silver staining (4A) and immunoblotting (4B).
Figure 4B:
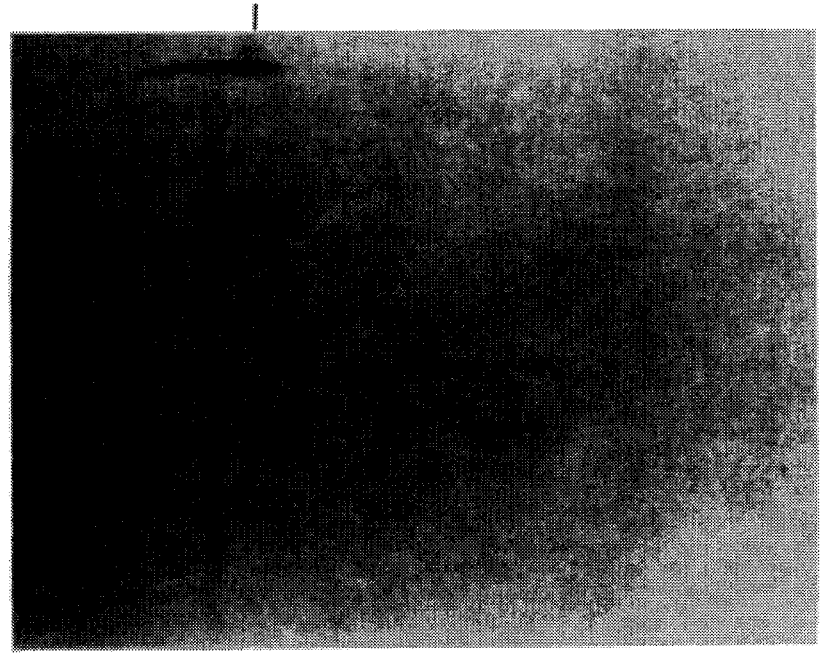

As a more stringent assessment of homogeneity, two dimensional gel electrophoresis (Dottin et al, 1979) was performed and analysed by silver staining and immunoblotting (FIG. 4). As in the 1-D gels no contaminating proteins were detected. The major isoelectric form of CFTR migrated at a position corresponding to a pI of approximately 9. This agrees well with the value of 8.98 calculated from the CFTR amino acid composition. Since only core, mannose-containing N-linked oligosaccharides are added to proteins in Sf9 cells (Vialand et al, 1990) carbohydrate would not be expected to influence the pI. The small immunoreactive spots may represent alternate isoelectric forms of CFTR.

The final purified protein was subjected to both N-terminal sequence determination and quantitative amino acid compositional analysis. The sequence of the N-terminal 6 residues agreed with that predicted from the DNA sequence for CFTR and there was excellent agreement between the amounts of each residue in the overall composition. The amino acid composition compared with that deduced from the sequence is shown in table II.

CFTR Reconstitution into phospholipid vesicles

In order to be able to determine the functional capacity of purified CFTR it was necessary to transfer the detergent solubilized protein back into a lipid environment. This was done by a dialysis protocol analogous to that employed for renaturation of bacteriorhodopsin (London and Khorana, 1982; Braiman et al, 1987) and some other transport proteins. Essentially, pure CFTR in 0.25% lithium dodecyl sulfate (LIDS) was mixed with a sonicated phospholipid mixture (PE:PS:PC at 5:2:1) containing 1% cholate and dialysed extensively to form proteoliposomes. Following dispersion by sonication, and concentration, these proteoliposomes were fused with liposomes of the same phospholipid composition but also containing ergosterol and nystatin to promote and enable detection of subsequent fusion to planar lipid bilayers (see below). This modification to enable the nystatin-induced liposome fusion was taken from Woodbury and Miller (1990). Following elution in the void volume of a Superose 12 gel filtration column, all of the CFTR employed in the reconstitution could be accounted for in immunoblots of the proteoliposomes.

Figure 5:
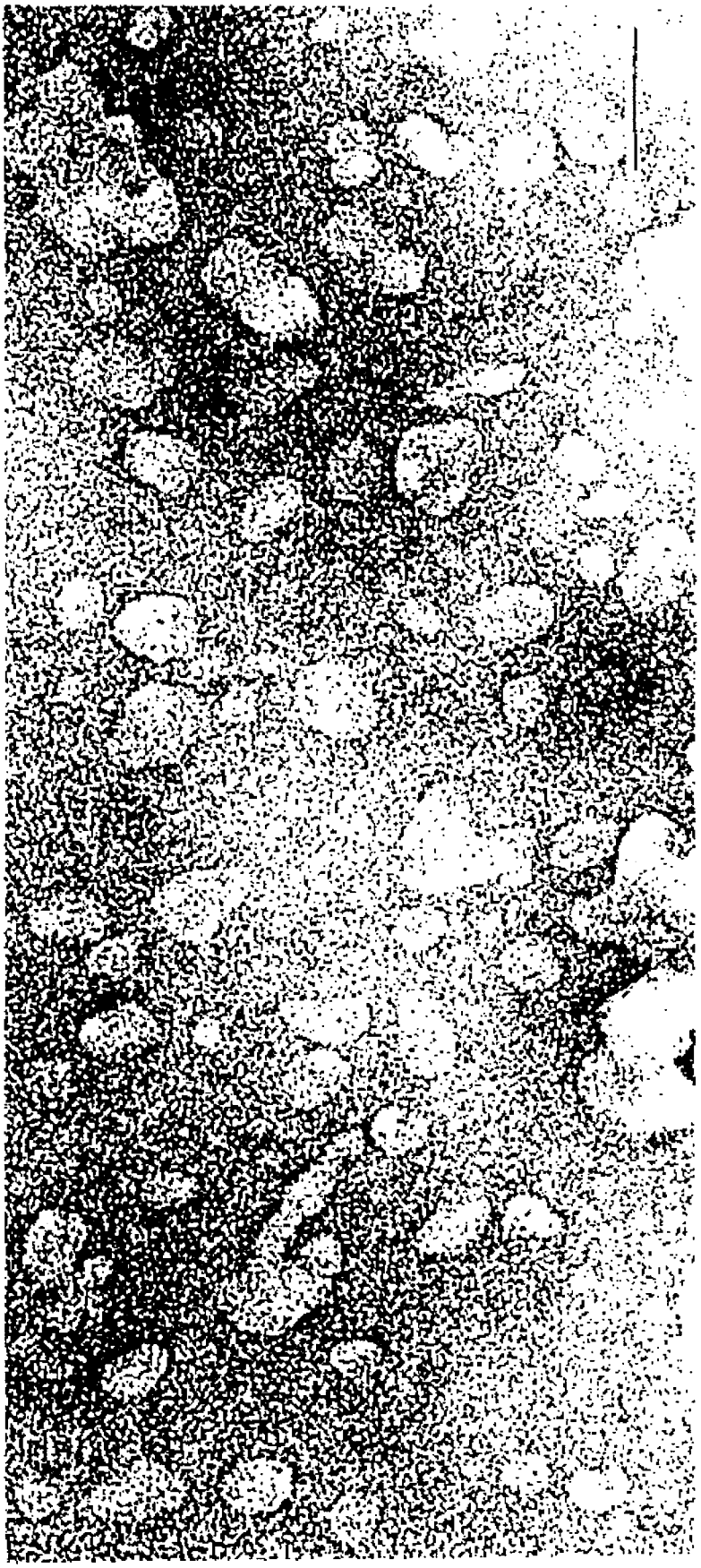
FIG. 5. Electronmicroscopy of negative stained proteoliposomes containing CFTR. Vesicles on carbon formvar coated grids were stained with 2% uranyl acetate. Scale is 0.1 μm.

Negative staining indicated a uniform population of CFTR containing proteoliposomes, about half of which have a diameter of 40–60 nm with the other half at approximately 15–20 nm (FIG. 5). Some fused larger vesicles were also present. The 5 nm vesicles would have a surface area of $7.9 \times 10^5$ Å$^2$. Using a value of 50 Å$^2$ for the average area occupied by a phospholipid molecule (Levitzki, 1985) there should be $1.6 \times 10^4$ phospholipid molecules per vesicle. Since we used 2 mg of phospholipid or $1.5 \times 10^{18}$ molecules approximately $10^{14}$ vesicles will have formed. These had incorporated 6.38 μg (based on quantitative amino acid analysis) corresponding to $3.8 \times 10^{-11}$ moles or $2.3 \times 10^{13}$ molecules of CFTR. Therefore, not more than one (approximately 0.23) CFTR had incorporated per 50 nm vesicle. The number of these vesicles which were subsequently fused to a black lipid film could then be monitored by the nystatin mediated conductance spikes (see below).

Effect of CFTR-containing proteoliposomes on a planar bilayer

Figure 6A:
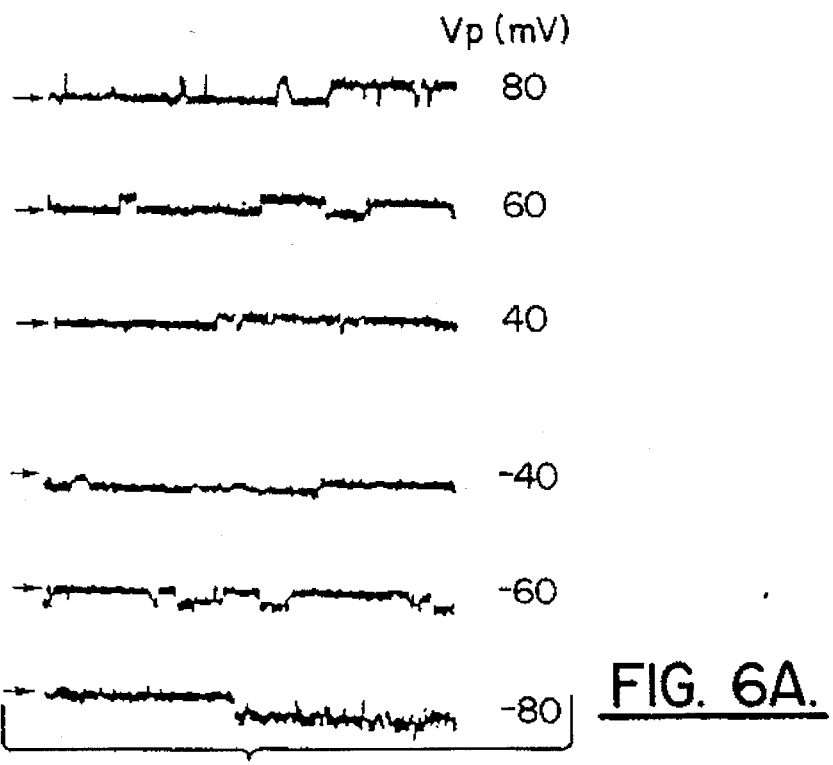
FIGS. 6A–6C. Low Conductance Cl⁻ Channel Associated with CFTR Expression in Sf9 Cells. (6A) This panel shows PKA-activated single channel current tracings at various pipette potentials in excised patches. The pipette and the bath contained symmetrical salt solutions (NaCl=140 mM). In addition, PKA (200 nM) and ATP (1 mM) were added to the bath to stimulate the appearance of this channel. (6B) Currents tracings from PKA-stimulated channels in excised membrane patch from CFTR-expressing Sf9 cell. In this case, channels were studied in the presence of 300 mM NaCl in the bath and 50 mM NaCl in the pipette. (6C) Current-voltage relationships are shown for PKA-stimulated channel in symmetrical NaCl solutions (bath and pipette=140 mM) (o) (n=8) and asymetrical NaCl solutions (bath=300 and pipette=50 mM NaCl) (•) (n=9). Means and SD have been shown. Arrows indicate the closed conductance state.
Figure 6B:
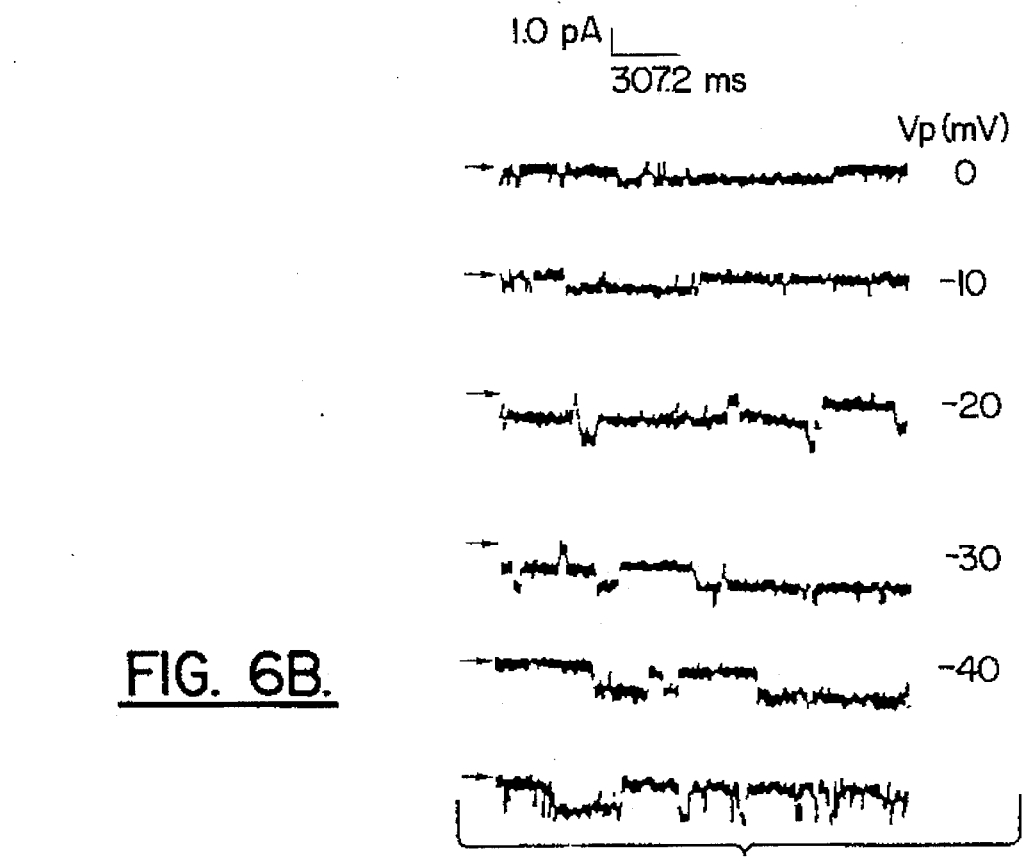
Figure 6C:
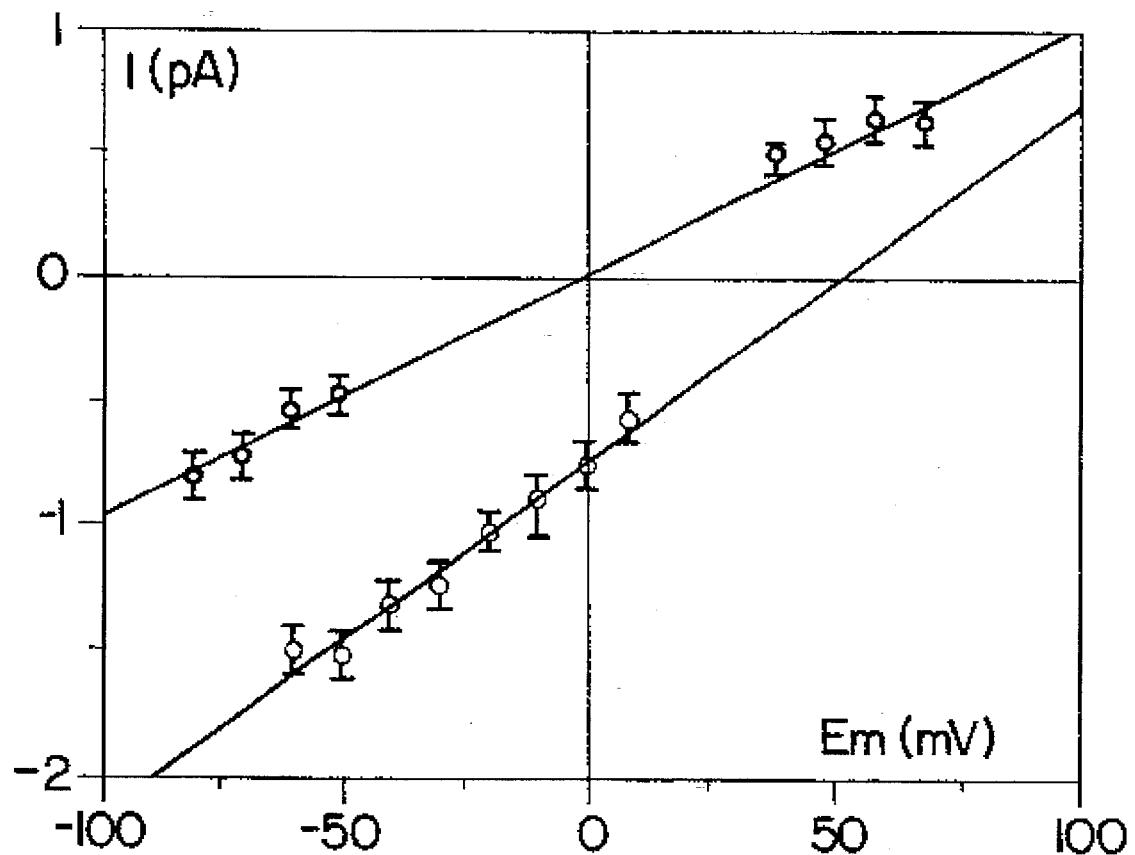

A cyclic AMP-activated, low-conductance chloride channel has been described in CFTR expressing Sf9 cells (Kartner et al., 1991). In order to compare the conductive properties of purified CFTR with that of the CFTR-associated channel in native membranes, it was first necessary to characterize this channel in Sf9 cell membranes under the same conditions which would later be dictated by the requirements of the planar bilayer. These conditions include an ionic gradient which is favorable for liposome fusion, i.e. the presence of an osmotic gradient (300 mm KCl versus 50 mm KCl). Therefore, the low conductance Cl$^-$ channel conductance in excised membrane patches from CFTR-expressing Sf9 cells was compared in symmetric and asymmetric ion gradients in order to assess the influence of these gradients on single ion conductance (FIG. 6).

No single channel activity corresponding to that of the low-conductance Cl$^-$ channel was detected in excised patches from CFTR-expressing Sf9 cells unless PKA (200 nM) and Mg-ATP (1 mM) were added to the bath. With the addition of PKA, a nonrectifying, 10.1 pS channel was detected with 140 mM NaCl in both the patch pipette and the bath (n=39). This observation supports the previous description of PKA regulation of the small, nonrectifying Cl$^-$ channel in excised patches of CHO cells expressing CFTR (Tabcharani et al., 1991). In the presence of an ion gradient comparable to that required for liposome fusion in planar bilayer studies, ie. 300 mM NaCl in the bath and 50 mM NaCl in the patch pipette (n=19), the current voltage (I-V) relationship of the PKA-regulated channel showed a shift in reversal potential to approximately 50 mV, a change consistent with high chloride selectivity, and an increase in unitary conductance to 14.1 pS. This relatively small change in conductance from 11 to 14 pS with a two fold increase in chloride concentration suggests that the effect of chloride concentration on unitary conductance is nonlinear. Tabcharani and Hanrahan have found that in excised patches from CHO cells expressing CFTR, the low conductance Cl$^-$ channel saturates as a function of Cl$^-$ activity with a Michaelis-Menten Km in the range of 35 to 40 mM.

In initial experiments with planar lipid bilayers, the CFTR-containing proteoliposomes were simply added to the cis chamber with mixing. Although indications of the appearance of Cl⁻ channel activity were detected early on, the fusion frequency was apparently low because the current changes eventually found to be characteristic of this channel in the bilayer were only observed infrequently (in 3 of 15 experiments) even in the presence of ATP and PKA. This made it difficult to be sure of the significance of the lack of activity under non-activating conditions. Therefore, we sought a means of both promoting and detecting fusion events. The nystatin fusion technique described just a year earlier by Woodbury and Miller (1990) seemed as if it should suit this purpose and was attempted. The rationale is that the ergosterol-nystatin complex which is incorporated into phospholipid vesicles during their formation provides non selective ionophore activity, thus generating an ionic and osmotic gradient which promotes fusion of the vesicles with the bilayer. When this occurs, a transient current spike is observed providing an index of the fusion events. Because nystatin renders essentially all vesicles fusogenic, the channel activity observed is representative of the whole population of vesicles. Since we had quantified the amount of CFTR in our vesicles, this technique provided a means of evaluating how much of it entered the bilayer. FIG. 7A shows a current tracing containing these spikes and the coincidence of a low conductance Cl⁻ current with one of them. On average this occurs once in 10 and 20 spikes. Since we had calculated that approximately one in four lipid vesicles contained a CFTR molecule after reconstitution, it appears that 20–40% of the purified protein molecules are capable of generating a channel in the bilayer.

Figure 7:
FIG. 7. Purified CFTR functions as a phosphorylation activated ion channel in lipid bilayers (a) The upper trace shows four nystatin spikes (o) which fail to lead to single channel activity. Two nystatin spikes are long lasting and two short lasting, the differences possibly reflecting stochastic variation in the number of nystatin units per liposome. Scale bars indicate 1 pA vertically and 5 sec horizontally. The lower trace shows a short lasting nystatin spike which is followed by the appearance of single chloride channel activity. PKA and Mg-ATP are present in both the cis and trans compartments. The scale bars indicate 1 pA vertically and 2 sec horizontally. Holding potential is –25 mV. (b) Addition of liposomes which do not contain purified CFTR to bilayer chamber with PKA (200 nM) and Mg₂ATP (1 mM) fails to cause appearance of unitary current steps. (c) Addition of liposomes containing CFTR with no added PKA and Mg₂ATP fails to evoke single channel activity. (d) Single channel activity is apparent only in those experiments in which CFTR-containing liposomes are added to the bilayer chamber with PKA and Mg₂ATP. The applied potential was –25 mV in this experiment.
Figure 7:
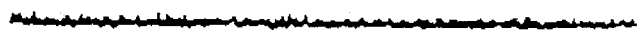
Figure 7:
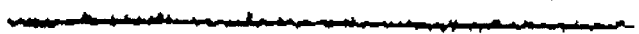
Figure 7:
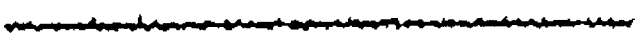
Figure 7:
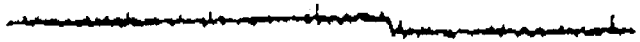
Figure 7:
Figure 7:
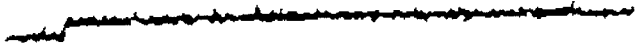
Figure 7:
Figure 7:
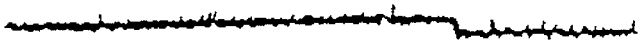
Figure 7:

FIGS. 7 B, C and D show records representative of many experiments to assess the relationships of the properties of the channel assayed in this way to those exhibited in the patch-clamp experiments with the cells from which CFTR had been purified. Fusion of liposomes without added CFTR (FIG. 7B) failed to produce the appearance of stepwise changes in current levels in the presence of PKA and Mg-ATP (added to both cis and trans compartment in all cases; n=6). Furthermore, fusion of CFTR-containing liposomes without added PKA and Mg-ATP (FIG. 7C) failed to evoke the appearance of single channel currents in 35 experiments in which fusion was achieved. Similarly, the addition of ATP alone, prior to PKA addition did not cause the appearance of single channel steps. Switch-like transitions in current level were only detected following fusion of CFTR containing liposomes in the presence of both PKA and ATP (FIG. 7D). Single channel events were observed in 35 of 45 experiments in which nystatin-induced fusion spikes were observed. Hence, in these experiments approximately 550 independent fusion events were detected and as a consequence 35 low conductance single channel events were detected. No single channel currents were detected in 10 of these 45 experiments due to problems of high noise and bilayer breakage. The mean open probability of the PKA stimulated channel was 0.38±0.13 for five experiments, a value close to that reported by Tabcharani et al (1991) for phosphorylation activated Cl⁻ channel in excised patches from CFTR-expressing CHO cells of 0.41.

Figure 8A:
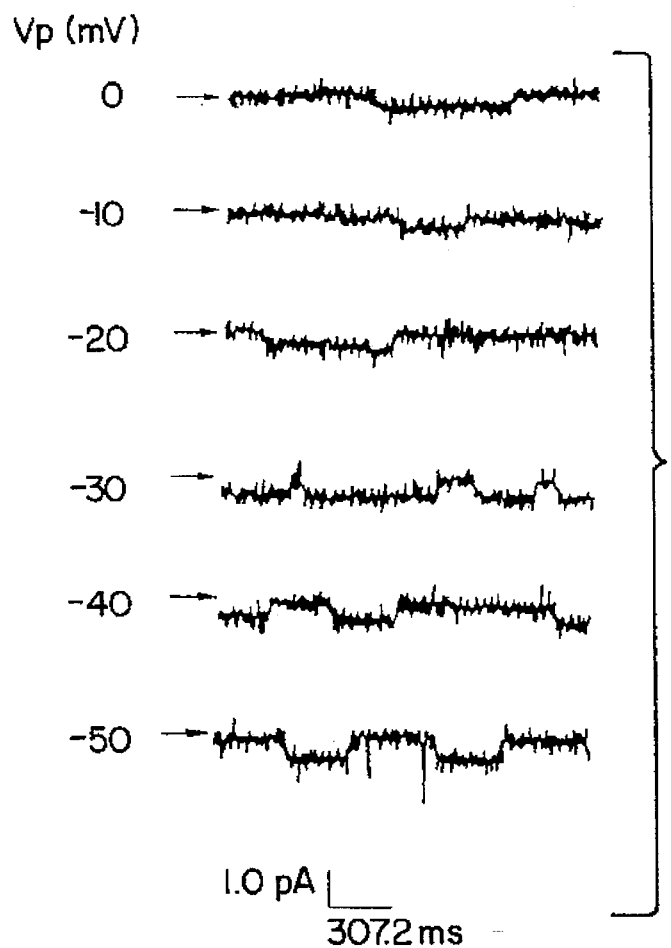
FIGS. 8A–8D. Comparison of current-voltage relationship of PKA-stimulated purified CFTR and Cl⁻ channel in T84 cells and CFTR-expressing CHO cells. (8A) Current traces are shown for purified CFTR protein in lipid bilayer at various potentials. The cis compartment of bilayer chamber contained 300 mM KCl, PKA (200 nM) and Mg-ATP (1 mM). The trans compartment contained 50 mM KCl+PKA and Mg-ATP. (8B) I-V relationships are shown for conductance of PKA-activated purified protein with 300 mM KCl in the cis compartment and 50 mM KCl (Δ) (n=6) or 10 mM KCl (o) (n=4) in the trans compartment. (8C) The upper panel shows two 11 pS channels opening sequentially in stepwise manner. The lower panel shows a larger conductance observed in the same recording which corresponds to twice the conductance of the more prevalent smaller conductance and may represent cooperative gating of two 11 pS channels. Holding potential was –45 mV. (D) I-V relationships for PKA-activated purified CFTR (o) (n=4), PKA-activated chloride channel in T84 (Δ) (n=4) and PKA-activated CFTR-expressing CHO (•) (n=4) membranes studied in planar lipid bilayers (cis:trans=300:10 mM KCl).
Figure 8B:
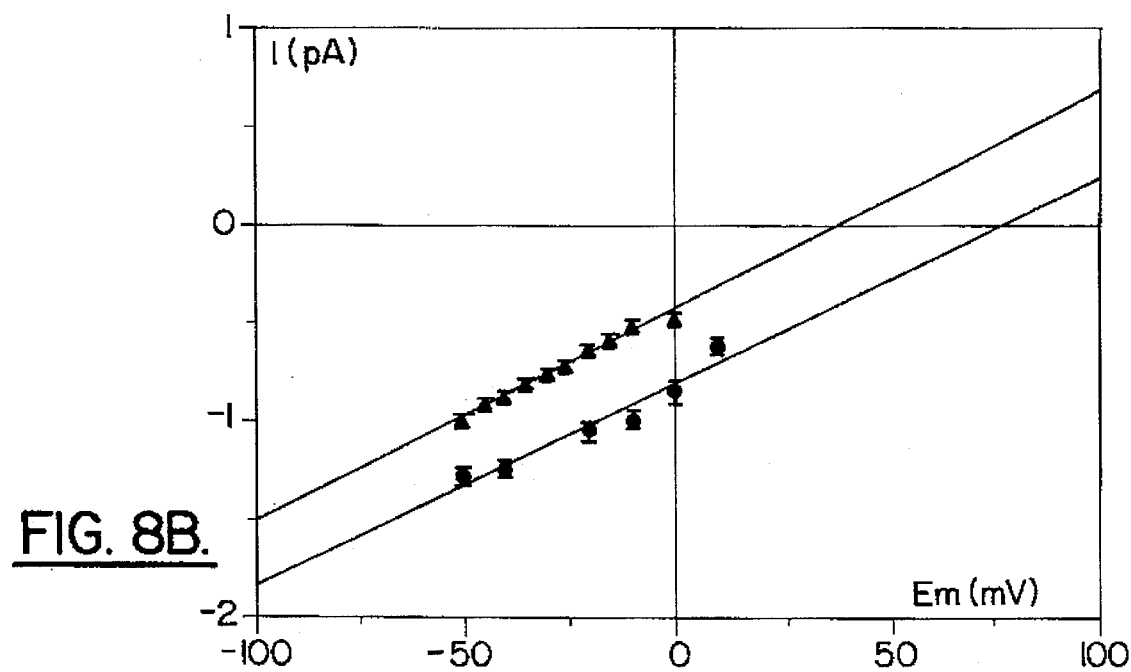

The current-voltage relationship of the reconstituted CFTR protein was found to be comparable to that observed for CFTR-expressing Sf9 membranes studied by the patch-clamp technique in the presence of similar ionic gradients. The slope conductance associated with the purified protein was 11.1 pS in the presence of 300 mM KCl in the cis compartment and 50 mM KCl in the trans compartment (FIGS. 8A and B). We observed no marked effect of voltage on channel open probability, a characteristic shared with the PKA-activated Cl⁻ channel studied in CFTR-expressing CHO cells (Tabcharani et al, 1991). The anion versus cation selectivity was estimated from the reversal potentials of the I-V curves. With 300 mM KCl on the cis side and 50 mM KCl on the trans side, one expects a reversal potential of 45 mV for an ideally anion selective channel. The extrapolated value obtained from 6 experiments was 39 mV. Furthermore, in the presence of the gradient (cis:trans=300:10) it is expected that current will reverse at 86 mV for an ideally anion selective conductance path. The extrapolated value from four experiments was 79 mV. We estimated using the Goldman-Hodgkin-Katz equation, therefore, that $Cl^-/K^+$ selectivity is at least 10:1. High chloride selectivity is another feature this channel shares with the CFTR-associated channel studied in CHO cells (Tabcharani et al, 1991).

Figure 8C:

Occasionally, in 4 of 35 experiments, another conductance level was detected in addition to the 11 pS conductance. This relatively rare conductance level corresponded to twice that of the predominant one and we believe that the larger conductance reflects cooperative gating of two 11 pS channels (FIG. 8C). Cooperative gating between different conductance states has been described for several purified channels, including the acetylcholine receptor (Schindler et al., 1984), bacterial porin (Engel et al, 1985) and the ryanodine receptor (Smith et al., 1988).

Figure 8D:
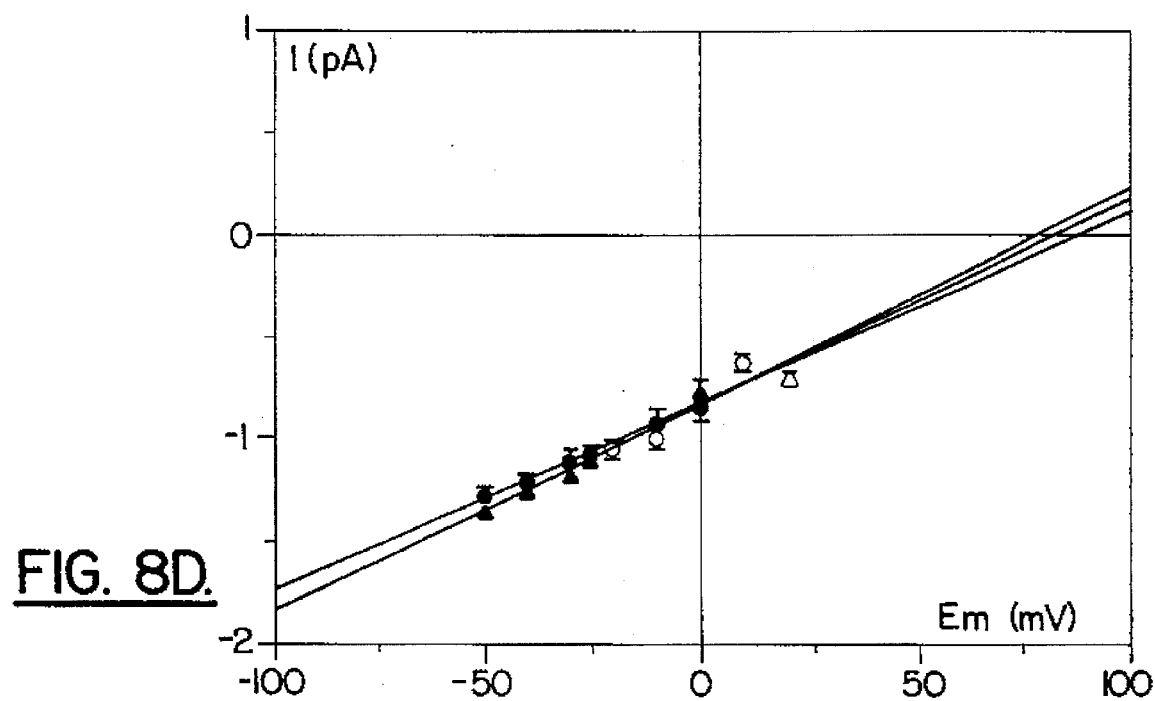

The identity of the conductance caused by purified CFTR incorporation into lipid bilayers with that present in cells which endogenously express CFTR, ie. T84 cells, and that conductance conferred by CFTR expression in CHO cell membranes, was confirmed in the experiments shown in FIG. 8D. The I-V relationships of the channels activated by PKA and ATP addition to purified CFTR, T84 and CFTR-containing CHO membranes following fusion with the lipid bilayer are virtually superimposable, showing similar unitary conductances (11.1 pS, 10.0 pS and 9.23 pS respectively) and reversal potentials (80 mV, 84 mV and 89 mV, respectively) in the presence of a 300/10 KCl gradient. Significantly, this PKA-activated chloride conductance was not observed following fusion of plasma membranes prepared from untransfected CHO cells with lipid bilayers. Only a relatively large conductance, approximately 40 pS, chloride channel was observed consistently when untransfected CHO cell membranes were used, but this channel was active both in the presence and in the absence of PKA. An identical phosphorylation—independent channel was also observed in CFTR-containing CHO cell membranes. This 40 pS channel is similar with respect to its conductance and rapid kinetics to that described by Reinhardt et al (1987) in bilayer studies of rat colonic apical membranes.

The inventors have demonstrated that a regulated Cl- channel with properties similar to that observed in intact cells can be detected in planar lipid bilayers into which highly purified CFTR is incorporated. The CFTR protein has been successfully removed from the membrane, manipulated extensively and returned to a functional state.

To address the question of the postulated Cl⁻ channel activity of CFTR, quantitative considerations are required. A channel activation was observed in black lipid films approximately once for every ten to twenty nystatin spikes reflecting the fusion of 10–20 vesicles. About one in four vesicles would contain a CFTR molecule (assuming a monomer although we have no evidence of this). This suggested that 20–40% of the reconstituted CFTR molecules may be capable of activation. This is an excellent degree of functional reconstitution given the type of solubilization, purification and reconstitution scheme used. However, these data also indicate that if channel activation required a protein other than CFTR it would have to be present in at least one copy per 5 CFTR molecules. The one and two dimensional gel electrophoresis data (FIGS. 1, 2 and 4) preclude the presence of 20% contamination. Furthermore, the fact that the purified protein yielded N-terminal amino sequence and overall amino acid composition indicative of the presence of only CFTR would argue that any contaminants which may be present must be in very low amounts, indicating that the protein of the invention is substantially homogeneous. Hence, we conclude that it is very likely that regulated channel activity is a property of the CFTR molecule itself. This invention presents the first functional characterisation of a purified epithelial channel.

Having the protein in isolation from others will assist, for example, in determining specific sites of interaction of modifying drugs such as sulfonyl ureas which in a preliminary report have recently been claimed to influence CFTR (Sheppard and Welsh, 1992).

In Cystic Fibrosis patients, the epithelial cells of many tissues, especially those of the lining of the airways, either lack CFTR in the cell membrane or have nonfunctional variants of the protein.

The isolation and purification of the CFTR protein, as in the present invention, makes possible therapy for Cystic Fibrosis patients, by restoring functional CFTR protein to the epithelial cells of the airways of the lung.

Proteins can be incorporated into cell membranes when they are supplied to the cell surface in association with a suitable carrier which assists the protein to be incorporated into the cell membrane, where it restores function. Suitable carriers will be known to those skilled in the art and include lipid vehicles such as the proteoliposomes of the present invention, which fuse with the cell surface allowing their contents to be incorporated into the cell membrane.

The protein plus carrier is administered to the epithelial cells to be treated by conventional means, for example by aerosol delivery to the airways of the lung.

Additional agents may be incorporated into the proteoliposomes to improve targeting towards a particular tissue, for example antibodies to particular cell surface molecules may be incorporated.

EXAMPLE 1

Cell Culture

Sf9 insect cells were infected with a recombinant Baculovirus containing the complete CFTR coding sequence as described previously (Kartner et al., 1991). For patch-clamp experiments cells were grown attached to plastic tissue culture dishes in Grace's media. For the purposes of protein purification, cells were gown in suspension culture. The human colonic carcinoma-derived epithelial cell line T84 (Dharmsathaphorn et al., 1984) was grown on a plastic substrate in 1:1 of Dulbecco's modified Eagle's medium and F-12 culture medium, and CHO cells expressing CFTR (Tabcharani et al, 1991) were grown in alpha modified minimal essential medium. All of these culture media were supplemented with 5 to 10% fetal bovine serum. Membrane preparations from T84 cells were obtained as described previously (Kartner et al, 1991) and highly purified plasma membrane vesicles were isolated from CHO cells according to Riordan and Ling (1979).

CFTR Purification

Sf9 cells from one liter of suspension culture were collected 3 days after infection yielding a 5 ml pellet which was resuspended and hypotonically swollen in 50 ml of 18 mM KCl, 5 mM sodium citrate, pH 6.8 (containing phenylmethyl sulfonyl fluoride at 100 μg/ml; aprotinin and leupeptin at 50 μg/ml). Cells were disrupted with a Potter-Elvejham homogenizer, particulates pelleted and treated with DNAase I (1 μg per mg total protein).

Mild alkaline extraction was performed for 2 minutes on ice with 20 volumes of 10 mM NaOH containing 0.1 mM EDTA.

The pelleted extracted material was dissolved in 10 mM phosphate buffer, pH 6.4 containing 2% mercaptoethanol and 2% SDS and was applied to a column (2.6×20 cm) of hydroxyapatite (Biogel HT, Biorad Laboratories) which had been preequilibrated with 10 mM phosphate buffer, pH 6.4 containing 0.15% SDS and 5 mM dithiothreitol (DTT). After washing with 50 ml of equilibration buffer, a 100 ml linear gradient (100 mM to 600 mM) of sodium phosphate containing 0.15% SDS and 5 mM DTT was applied at a flow rate of 0.2 ml per minute. Elution was continued with the high phosphate buffer for an additional 100 ml at a flow rate of 0.1 ml per minute. Absorbance was monitored continuously at 280 nm and aliquots of each fraction were monitored for CFTR by dot blots on nitrocellulose probed with the monoclonal antibody M3A7. Positive fractions were further assayed by SDS-PAGE and immunoblotting.

CFTR-containing fractions from the hydroxyapatite column were transferred to Centricon centrifugal microconcentrator tubes (Amicon) with a 30 kd cutoff, washed with 10 mM Tris-HCl, pH 8.0 containing 100 mM NaCl and 0.25% LiDS (lithium dodecyl sulfate) also in these devices and again concentrated to 400 μl. This volume was applied to a Superose 6 preparative FPLC column (Pharmacia) pre-equilibrated with this same buffer. Fractions eluted from the Superose 6 column were monitored as with the hydroxyapatite column.

CFTR Protein Detection end Characterization

One dimensional SDS-PAGE was according to Laemmli (1970) using 6% acrylamide gels as described previously (Kartner et al, 1991) or 4 to 15% gradient gels. Two dimensional gel electrophoresis was performed according to Dottrin et al (1979). Total proteins in either type of gel were stained with silver (Merril et al, 1981). Immunoblotting was as described previously employing a monoclonal antibody (M3A7) generated against a fusion protein containing residues 1197–1480 of CFTR.

CFTR Reconstitution into Phospholipid Vesicles

100 μl of 15 mM HEPES, 0.5 mM EGTA, pH 7.4 containing 1 mg of a sonicated phospholipid mixture (PE:P-S:PC/5:2:1) and 2% sodium cholate was added to 100 μl of 10 mM Tris-HCl, pH 8.0 containing 100 mM NaCl, 0.25% LiDS and 5 μg of purified CFTR. After a one hour incubation on ice the mixture was dialysed at 4° C. against 2 liters of the HEPES-EDTA buffer for 5 days with daily buffer changes. The sample was further dialysed for 3 days against daily changes of 2 liters of the same buffer containing 150 mM NaCl. The proteoliposomes thus obtained were sonicated for 15 seconds in a bath sonicator from Lab Supplies Co. Inc., Hicksville, N.Y. 11801 (Model Gl128PlG) and concentrated to 100 μl in a Minicon B15 concentrator (Amicon). To introduce nystatin according to the procedure of Woodbury and Miller (1990), this 100 μl sample was mixed with 100 μl of protein-free liposomes which had been prepared by sonicating a mixture of PE:PS:PC:Ergosterol at a ratio of 5:2:1:2 (10 mg/ml) in the presence of 120 μg/ml nystatin in the HEPES-EGTA buffer containing 300 mM NaCl. The mixture was frozen and thawed and sonicated for 15–20 sec. This cycle was repeated and the final proteoliposomes either used immediately for fusion with planar bilayers or frozen at −85°. In the latter case aliquots were thawed and sonicated briefly before use. The presence of intact CFTR was verified by exclusion from a Superose 12 column (Pharmacia).

For estimation of their diameters, the proteoliposomes were pipetted onto carbon formvar-coated grids, then negatively stained with 2% aqueous uranyl acetate and viewed and photogaphed by transmission electron microscopy.

Incorporation of CFTR into Planar Bilayers

A 10 mg/ml solution of phospholipid (PE:PS at a ratio of 7:3) (Avanti Polar Lipids) in n-decane was painted over a 200 μm aperature in a bilayer chamber to raise phospholipid bilayers. Bilayer formation was monitored electrically by observing the increase in membrane capacitance. In all experiments, bilayer capacitance was greater than 200 pF.

The solution in the cis compartment (where proteoliposomes were added) typically contained 300 mM KCl, 10 mM MOPS, 1 mM $MgCl_2$ and 2 mM $CaCl_2$, pH=6.9. The trans solution contained 50 mM KCl, 10 mM MOPS, 1 mM $MgCl_2$ and 2 mM $CaCl_2$, pH 6.9. Single channel currents were detected with a patch-clamp amplifier, modified for bilayer studies (Warner Instruments) and recorded following digitization (PCM2, Medical Systems) using a VCR. For playback of records, a 6-pole Bessel filter was used (100 Hz). Single channel current amplitudes were determined by the generation of amplitude histograms using pCLAMP software. Open-state probability was determined using the same software program and openings were defined using the 50% threshold criterion.

Addition of 4 μl of proteoliposomes preparation to the cis compartment of the bilayer chamber, followed by stirring (approximately 10 min) typically resulted in the appearance of 10–20 abrupt conductance steps or spikes, indicative of fusion of roughly 10–20 liposomes with the lipid bilayer. The conductance steps are due to current flow through ergosterol-dependent nystatin channels and the transient nature of these steps reflects the dissociation of the ergosterol-nystatin complex as the liposome composition diffuses into the ergosterol-free bilayer. Cessation of stirring prevented further liposome fusion with no further appearance of spikes. The incorporation of a channel with liposome fusion was detected as a stepwise change in current level. Membrane potentials were referenced to the trans compartment and $Cl^-$ current from cis to trans designated as negative.

Patch-Clamp Studies of CFTR-expressing cells

Single channel currents were recorded using conventional procedures according to Hamill et al (Hamill et al, 1981) with a List EPC-7 patch-clamp amplifier (Medical Systems, Great Neck, N.Y.) Pipettes were fabricated from borosilicate glass type 7052 (Gamer Glass Co.) using a two-stage Narishige pipette puller. The bath electrode was a Ag-AgCl wire connected to the bathing solution via an agar bridge. Current output was monitored on a Tektronix oscilloscope and stored on videotape after A/D conversion by a video adaptor (PCM 2, Medical Systems). Single channel current records stored on video tape were transferred to the hard disk of an EBM-AT compatible computer using the FETCHEX program of pCLAMP (Version V) software (Axon Inst.) Records were sampled at 0.5–2.0 kHz. During playback, single channel records were filtered using a 6-pole Bessel filter set at 100 or 200 Hz low pass frequency. Single channel current amplitudes were obtained by examination of amplitude histograms generated using the pCLAMP FETCHAN analysis program. The mean of the peak amplitude was taken as a measure of the unitary current amplitude.

Solutions: In excised patch studies the standard bath and pipette solutions contained 140 mM NaCl, 1 mM $MgCl_2$, 2 mM $CaCl_2$, 10 mM glucose and 10 mM MES, pH 6.3. In some studies, the pipette solution contained 50 mM NaCl plus sucrose (added to adjust osmolarity to 280 mOsm) and the bath solution contained 300 mM NaCl. Experiments were performed at 22°–25° C.

REFERENCES

Anderson, M. P., Rich, D. P., Gregory, R. J., Smith, A. E. and Welsh, M. J. (1991a).
Generation of cAMP-activated chloride currents by expression of CFTR. Science 25 1, 679–682.
Anderson, M. P., Gregory, R. J., Thompson, S., Souza, D. W., Paul, S., Mulligan, R. C., Smith, A. E. and Welsh, M. J. (1991b). Demonstration that CFTR is a chloride channel by alteration of its anion selectivity. Science 253, 202–205.
Anderson, M. P., Berger, H. A., Rich, D. P., Gregory, R. J., Smith, A. E. and Welsh, M. J. (1991c). Nucleoside triphosphates are required to open the CFTR chloride channel. Cell 67, 775–784.
Bear, C., Duguay, F., Naismith, A. L., Kartner, N., Hanrahan, J. W. and Riordan, J. R. (1991). Cl- channel activity in Xenopus oocytes expressing the cystic fibrosis gene. J. Biol. Chem. 266, 19142–19145.
Berger, H. B., Anderson, M. P., Gregory, R. J., Thompson, S., Howard, P. W., Maurer, R. A., Mulligan, R., Smith, A. E. and Welsh, M. J. (1991). Identification and regulation of the CFTR-generated chloride channel. J. Clin. Invest. 88, 1422–1431.
Braiman, M. J., Stem, L. J., Chao, B. H. and Khorana, H. G. (1987). Structure-function studies of bacteriorhodopsin. J. Biol. Chem. 262-9271–9276.
Cheng, S. H., Gregory, R. J., Marshall, J., Paul, S., Souza, D. W., White, G. A., O'Riordan, C. R. and Smith, A. E. (1990). Defective intracellular transport and processing of CFTR is the molecular basis of most cystic fibrosis. Cell 63, 827–834.
Dalemans, W., Barbry, P., Champigny, G., Jallat, S., Dott, K., Dreyer, D., Crystal, R. G., Pavarani, A., Lecocq, J-P and Lazdunski, M. (1991). Altered chloride ion channel kinetics associated with the AF508 cystic fibrosis mutation. Nature 354, 526–528.
Dharmsathaphon, K., McRoberts, J. A., Mandel, K. G., Tisdale, L. D. and Masui, H. (1984). A human colonic tumor cell line that maintains vectorial electrolyte transport. Amer. J. Physiol. 246, G204–G208.
DiTullio, P., Cheng, S. H., Marshall, J., Gregory, R. J., Ebert, K. M., Meade, H. M. and Smith, A. E. (1992) Production of Cystic Fibrosis Transmembrane Conductance Regulator in the Milk of Transgenic Mice. Biotechnology 10: 74–77.
Dottin, R. P., Manrow, R. E., Fishel, B. R., Aukerman, S. L. and Culleton, S. L. (1979). Localization of enzymes in denaturing polyacrylamide gels. Methods Enzymol. 68, 513–527.

Drumm, M. L., Pope, H. A., Cliff, W. H., Rommens, J. M., Marvin, S. A., Tsui, L.-C., Collins, F. S., Frizzell, R. A. and Wilson, J. M. (1990). Correction of the cystic fibrosis defect in vitro by retrovirus-mediated gene transfer. Cell 62, 1227–1233.

Drumm, M. L., Wilkinson, D. S., Smit, L. S., Worrell, R. T., Strong, T. V., Frizzell, R. A., Dawson, D. C. and Collins, F. S. (1991). Chloride conductance expressed by F508 and other mutant CFTRs in Xenopus oocytes. Science 254, 1797–1799.

Engel, A., Massalski, A., Schindler, H., Dorset, D. L. and Rosenbusch, J. P. (1985). Porin channel triplets merge into single outlets in Escherichia coli outer membranes. Nature (London) 317, 643–645.

Flem, K., Perez, A., Culp, L. and Davis, P. (1991). Overexpression of R domain reduces basal chloride conductance and eliminates cAMP stimulated chloride secretion in 9/HTE ocells. Late Breaking Science Session of North American Cystic Fibrosis Conference, Dallas, Tex., Oct. 2–5, 1991.

Furman, R. E., Tanaka, J. C., Mueller, P. and Barchi, R. L. (1986). Voltage-dependent activation in purified reconstituted sodium channels from rabbit T-tubular membranes. Proc. Natl. Acad. Sci. USA 83, 488–492.

Gray, M. A., Harris, A., Coleman, L., Greenwell, J. R. and Argent, B. E. (1989). Two types of chloride channel on duct cells cultured from human fetal pancreas. Am. J. Physiol. 257, C240–C251.

Gregory, R. J., Rich, D. P., Cheng, S. H., Souza, D. W., Paul, S., Manavalan, P., Anderson, M. P., Welsh, M. J. and Smith, A. E. (1991). Maturation and function of cystic fibrosis transmembrane conductance regulator variants bearing mutations in putative nucleotide-binding domains 1 and 2. Mol. Cell. Biol. 11, 3886–3893.

Hamill, O. P., Marty, A., Neher, E., Sakman, B. and Sigworth, F. J. (1981) Improved patch-clamp techniques for high-resolution current recording from cells and cell-free membrane patches. Pfluegers Arch. 391, 85–100.

Hartshore, R. P., Keller, B. O., Talvenheimo, J. A., Catterall, W. A. and Montal, M. (1985). Functional reconstitution of the purified brain sodium channel in planar lipid bilayers. Proc. Natl. Acad. Sci. USA 82, 240–244.

Kartner, N., Hanrahan, J. W., Jensen, T. J., Naismith, A. L., Sun, S., Ackerley, C. A., Reyes, E. F., Tsui, L.-C., Rommens, J. M., Bear, C. E. and Riordan, J. R. (1991). Expression of the cystic fibrosis gene in non-epithelial invertebrate cells produces a regulated anion conductance. Cell 64, 681–691.

Kerem, B.-S., Rommens, J. M., Buchanan, J.-A., Markiewicz, D., Cox, T. K., Chakravarti, A., Buchwald, M. and Tsui, L.-C. (1989) Identification of the Cystic Fibrosis Gene: Genetic Analysis. Science 245: 1073–1080.

La, Bao-Quoc, Carosi, S. L., Valentich, J., Shenolikar, S. and Sansom, S. C. (1991) Regulation of epithelial chloride channels by protein phosphatase. Am. J. Physiol. 260, C1217–C1233.

Laemmli, U. K. (1970). Cleavage of structural proteins during the assembly of the head of bacteriophage T4. Nature 227, 680–685.

Levitzki, A. (1985). Reconstitution of membrane receptor systems. Biochim. Biophys. Acta 822, 127–153.

London, E. and Khorana, H. Gobind (1982). Denaturation and renaturation of bacteriorhodopsin in detergents and lipid-detergent mixtures. J. Biol. Chem. 257, 70037011.

Luckow, V. A. and Summers, M. D. (1988). Trends in the development of baculovirus expression vectors. Bio/Technol 6, 47–55.

Merril, C. R., Goldman, D., Sedman, J. A. and Ebert, M. H. (1981). Ultrasensitive stain for proteins in polyacrylamide gels shows regional variation in cerebrospinal fluid proteins. Science 211, 1437–1438.

Montal, M., Labarca, P., Fredkin, D. R., Suarez-Isla, B. A. and Lindstrom, J. (1984). Channel properties of the purified acetylcholine receptor from Torpedo californica reconstituted in planar lipid bilayer membranes. Biophys. J. 45, 165–174.

Nowak, R. (1991). CFTR: It's a pump, it's a channel, it's a little of each. J.NIH Res. 3, 30–31.

Reinhardt, R., Bridges, R. S., Rummel, W. and Lindemann, B. (1987) Properties of an anion-selective channel from rat colonic enterocyte plasma membranes reconstituted into planar phospholipid bilayers. J. Membrane Biol. 95, 47–54.

Rich, D. P., Anderson, M. P., Gregory, R. J., Cheng, S. H., Paul, S., Jefferson, D. M., McCann, J. D., Klinger, K. W., Smith, A. E. and Welsh, M. J. (1990). Expression of cystic fibrosis transmembrane conductance regulator corrects defective chloride channel regulation in cystic fibrosis airway epithelial cells. Nature 347, 358–363.

Rich, D. P., Gregory, R. J., Anderson, M. P., Manavalan, P., Smith, A. E. and Welsh, M. J. (199 1). Effect of deleting the R domain on CFTR-generated chloride channels. Science 253, 205–207.

Riordan, J. R. and Ling, V. (1979). Purification of P-glycoprotein from plasma membrane vesicles of Chinese hamster ovary cell mutants with reduced colchicine permeability. J. Biol. Chem. 254, 12701–12705.

Riordan, J. R., Rommens, J. M., Kerem, B-S, Alon, N., Rozmahel, R., Grzelczak, Z., Zielenski, J., Lok, S., Plavsic, N., Chou, J-L, Drumm, M. L., Iannuzzi, M. C., Collins, F. S. and Tsui, L.-C. (1989). Identification of the Cystic Fibrosis Gene: Cloning and characterization of complementary DNA. Science 245, 1066–1073.

Riordan, J. R., Alon, N., Grzelczak, Z., Dubel, S. and Sun, S. (1991). The CF gene product as a member of a membrane transporter (TM6-NBF) super family. Adv. Exp. Med. Biol. 290: 19–29.

Rommens, J. M., Iannuzzi, M. C., Kerem, B-S, Drumm, M. L., Melmer, G., Dean, M., Rozmahel, R., Cole, J. L., Kennedy, D., Hidaka, N., Zsiga, M. Buchwald, M., Riordan, J. R., Tsui, L.-C. and Collins, F. (1989) Identification of the Cystic Fibrosis gene: Chromosome walking and jumping. Science 245: 1059–1065.

Sariban-Sohraby, S., Latorre, R., Burg, M., Olans, L. and Benos, D. (1984). Amiloridesensitive epithelial Na+ channels reconstituted into planar lipid bilayer membranes. Nature (London) 308, 80–82.

Schindler, H., Spillecke, P. and Neumann, E. (1984). Different channel properties of Torpedo acetylcholine receptor monomers and dimers reconstituted in planar membranes. Proc. Natl. Acad. Sci. USA 81, 6222–6226.

Sheppard, D. N. and Welsh, M. J. (1992). Effect of K-ATP channel regulators on CFTR Cl⁻ currents. FASEB J. 6, A537.

Smith, J. S., Imagawa, T., Ma, J., Fill, M., Campbell, K. P. and Coronado, R. (1988). Purified ryanodine receptor from rabbit skeletal muscle is the calcium-release channel of sarcoplasmic reticulum. J. Gen. Physiol. 92, 1–26.

Steck, T. L. and Yu, J. (1973) Selective solubilization of proteins from red blood cell membranes by protein perturbants. J. Supramol. Structure 1, 220–232

Tabcharani, J. A., Low, D., Elie, D. and Hanrahan, J. W. (1990). Low-conductance chloride channel activated by cAMP in the epithelial cell line T84. FEBS Lett. 270, 157164.

Tabcharani, J. A., Chang, X.-B., Riordan, J. R. and Hanrahan, J. W. (1991). Phosphorylation-regulated Cl channel in CHO cells stably expressing the cystic fibmsis gene. Nature 352, 628–631.

Valdivia, H. H., Dubinsky, W. P. and Coronado, R. (1988). Reconstitution and phosphorylation of chloride channels from airway epithelium membranes. Science 242, 1441–1444.

Vialard, J., Lalumiere, M., Venet, T., Briedis, D., Alkhatib, G., Henning, D., Levin, D. and Richardson, C. (1990). Synthesis of the membrane fusion and hemagglutinin proteins of measles virus using a novel baculovirus vector containing the B-galactosidase gene. J. Virol. 64, 37–50.

Woodbury, D. J. and Miller, C. (1990). Nystatin-induced liposome fusion. A versatile approach to ion channel reconstitution into planar bilayers. Biophys. J. 58, 833–839.

TABLE I

Protein Recovery during CFTR Purification

| Step | Total protein (mg) | Enrichment factor* |
|---|---|---|
| Particulate pellet | 300 | 1 |
| After alkali extraction | 105 | 2.9 |
| After hydroxyapatite | 1.0 | 300 |
| After Superose 6 | 0.5 | 600 |

Starting material was a one liter culture containing approximately $5 \times 10^9$ cells.
*assuming no loss of CFTR.

TABLE II

Amino Acid Composition

| Residues | Predicted* | Determined | Ratio Determined/ Predicted |
|---|---|---|---|
| Asx | 113 | 100 | 0.88 |
| Glx | 160 | 154 | 0.96 |
| Ser | 122 | 127 | 1.04 |
| Gly | 84 | 84 | 1.00 |
| His | 24 | 24.4 | 1.01 |
| Arg | 78 | 76.4 | .98 |
| Thr | 83 | 86.6 | 1.04 |
| Ala | 83 | 83 | 1.00 |
| Pro | 45 | 42 | 0.93 |
| Tyr | 40 | nd | |
| Val | 89 | 89.3 | 1.00 |
| Met | 38 | 36 | 0.95 |
| Cys | 18 | 20.8 | 1.15 |
| Ile | 120 | 113 | 0.94 |
| Leu | 18 | 181.2 | 0.98 |
| Phe | 84 | 82.8 | 0.99 |
| Lys | 92 | 96.8 | 1.05 |

*from sequence
nd - not determined
1.5 µg of protein was hydrolysed with 6N HCl, PITC derivatized and separated by HPLC on a PICOTAG column (Waters Associates).

The embodiments of the invention in which an exclusive property or privilege is claimed are defined as follows:

1. A substantially homogeneous protein having cystic fibrosis transmembrane conductance regulator activity and characterised by migration as a single band on both one- and two-dimensional gel electrophoresis.

2. A protein in accordance with claim 1 and having the determined amino acid composition set out in Table II.

3. A protein in accordance with claim 1 and specifically recognized by monoclonal antibodies to cystic fibrosis transmembrane conductance regulator (CFTR).

4. A protein in accordance with claim 1 and having the N-terminal amino acid sequence: Met Gln Arg Ser Pro Leu.

5. A protein in accordance with claim i and having an empirically determined isoelectric point of approximately 9.

6. A protein in accordance with claim 1 and having the ability to generate an ohmic chloride channel having a unitary conductance of approximately 10 to 14 pS when activated by protein kinase A.

7. A protein in accordance with claim 1 having a secondary, tertiary and quaternary structure which can be determined by physical biochemistry methods.

8. A therapeutically effective composition for treating a subject having cystic fibrosis by aerosol delivery of a therapeutic agent to the airways of the subject, said composition comprising a therapeutic agent comprising a protein in accordance with any of claims 2 to 7 and a carrier suitable for aerosol delivery of said protein to cells of the airways of said subject having deficient CFTR function.

9. A therapeutically effective composition for the treatment of cystic fibrosis, in accordance with claim 8, wherein the composition may be delivered to a subject's airways.

10. A method for treating a subject with cystic fibrosis comprising delivering a therapeutically effective composition in accordance with claim 8 to the airway passages of a subject by aerosol delivery.

11. A therapeutically effective composition for treating a subject having cystic fibrosis by aerosol delivery of a therapeutic agent to the airways of the subject, said composition comprising a therapeutic agent comprising a protein in accordance with claim 1 and a carrier suitable for aerosol delivery of said protein to cells of the airways of said subject having deficient CFTR function.

12. A therapeutically effective composition in accordance with claim 11 wherein said carrier is a lipid vehicle.

13. A therapeutically effective composition in accordance with claim 12 wherein said carrier is a proteoliposome.

14. A method for purifying a recombinant hydrophobic membrane protein comprising the steps of:

(a) providing a sample of cells containing a membrane—associated protein to be purified;

(b) disrupting the cells and pelleting a particulate fraction thereof;

(c) contacting the particulate fraction with a dilute alkali solution for an effective period of time at an effective temperature to extract unwanted constituents followed by repelleting the particulate fraction;

(d) dissolving the particulate fraction in a buffered denaturing detergent solution containing a thiol reducing agent;

(e) subjecting the solution obtained by step (d) to hydroxyapatite chromatography to provide a partially purified protein;

(f) subjecting the partially purified protein obtained by step (e) to molecular sieve chromatography to provide a substantially homogeneous protein; and (g) renaturing the protein obtained by step (f) by competitively removing sodium dodecyl sulphate from association with the protein by exposure to excess sodium cholate and removing sodium cholate and sodium dodecyl sulphate by dialysis in the presence of phospholipid whereby the protein is incorporated into phospholipid vesicles to provide a functional protein.

15. A method in accordance with claim 14 wherein the membrane-associated protein is cystic fibrosis transmembrane conductance regulator and wherein step (d) comprises dissolving the particulate fraction in 2% sodium dodecyl sulphate (SDS) and 2% mercaptoethanol in 10 mM phosphate buffer of pH 6.4, step (e) comprises applying the solution from step (d) to a hydroxyapatite column pre-equilibrated with 10 mM phosphate buffer of pH 6.4 containing 0.15% SDS and 5 mM dithiothreitol (DTT), washing the column with the same buffer and eluting the protein with a phosphate buffer gradient containing 0.15% SDS and 5 mM DTT; step (f) comprises chromatography on a Superose 6 preparative FPLC column in a suitable buffer containing 0.25% lithium dodecyl sulphate (LIDS); and step (g) comprises combining a first solution containing the purified protein from step (f) in a buffer with a second solution containing a sonicated phospholipid mixture and 2% sodium cholate in a buffer, incubating the combined solution on ice for an effective period of time and dialysing the combined solution against a buffer for an effective period of time to give proteophospholipid vesicles.

* * * * *

UNITED STATES PATENT AND TRADEMARK OFFICE
CERTIFICATE OF CORRECTION

PATENT NO. : 5,543,399
DATED : August 6, 1996
INVENTOR(S) : Riordan et al.

It is certified that error appears in the above-indentified patent and that said Letters Patent is hereby corrected as shown below:

TITLE PAGE:
Page 2, column 1, References, line 34, "370" should be -- 870 --.

Page 4, column 1, References, line 11, "Chloried" should be -- Chloride --.

Page 4, column 1, References, line 23, "122" should be -- q22 --.

Column 2, line 39, "Druman" should be -- Drumm --.

Column 6, line 11, "5" should be -- 50 --.

Column 10, line 41, in the subheading, "end" should be -- and --.

Column 16, line 3, "i" should be -- 1 --.

Signed and Sealed this

Twenty-first Day of January, 1997

Attest:

BRUCE LEHMAN

*Attesting Officer*   *Commissioner of Patents and Trademarks*